US008932812B2

(12) United States Patent
Hogers et al.

(10) Patent No.: US 8,932,812 B2
(45) Date of Patent: Jan. 13, 2015

(54) RESTRICTION ENZYME BASED WHOLE GENOME SEQUENCING

(75) Inventors: René Cornelis Josephus Hogers, Wageningen (NL); Michael Josephus Theresia van Eijk, Wageningen (NL)

(73) Assignee: KeyGene N.V., Wageningen (NL)

( * ) Notice: Subject to any disclaimer, the term of this patent is extended or adjusted under 35 U.S.C. 154(b) by 207 days.

(21) Appl. No.: 13/320,379

(22) PCT Filed: Dec. 16, 2010

(86) PCT No.: PCT/NL2010/050854
§ 371 (c)(1),
(2), (4) Date: Jan. 5, 2012

(87) PCT Pub. No.: WO2011/074960
PCT Pub. Date: Jun. 23, 2011

(65) Prior Publication Data
US 2012/0245037 A1 Sep. 27, 2012

Related U.S. Application Data

(60) Provisional application No. 61/287,440, filed on Dec. 17, 2009.

(30) Foreign Application Priority Data

Dec. 22, 2009 (NL) .................................. 2004005

(51) Int. Cl.
C12Q 1/68 (2006.01)
C07H 21/00 (2006.01)
(52) U.S. Cl.
CPC ................... *C12Q 1/6869* (2013.01)
USPC .......................... 435/6.1; 536/22.1
(58) Field of Classification Search
CPC .................. C12Q 1/68; C12Q 1/6869
USPC .......................... 435/6.1; 536/22.1
See application file for complete search history.

(56) References Cited

U.S. PATENT DOCUMENTS

| 2001/0049438 | A1* | 12/2001 | Dix et al. ................... 536/25.4 |
| 2002/0182630 | A1 | 12/2002 | Milosavljevic |
| 2003/0059815 | A1 | 3/2003 | Sapolsky et al. |
| 2003/0224439 | A1* | 12/2003 | Lafferty et al. ................... 435/6 |
| 2004/0082001 | A1* | 4/2004 | Macevicz ........................ 435/6 |
| 2007/0082358 | A1 | 4/2007 | Fuerst et al. |
| 2007/0092884 | A1* | 4/2007 | Cole et al. ......................... 435/6 |
| 2009/0029377 | A1* | 1/2009 | Lo et al. ........................... 435/6 |
| 2011/0033920 | A1* | 2/2011 | Hartley et al. ............. 435/320.1 |
| 2013/0196859 | A1* | 8/2013 | Van Eijk et al. ................... 506/2 |

FOREIGN PATENT DOCUMENTS

| WO | WO 03/027311 A2 | 4/2003 |
| WO | WO 03/050242 A2 | 6/2003 |
| WO | WO 2007/073165 A1 | 6/2007 |
| WO | WO 2007/145612 A1 | 12/2007 |
| WO | WO 2008/007951 A1 | 1/2008 |
| WO | WO 2009/032167 A1 | 3/2009 |
| WO | WO 2010/082815 A1 | 7/2010 |

OTHER PUBLICATIONS

Aury et al., High quality draft sequences for prokaryotic genomes using a mix of new sequencing technologies. BMC Genomics 9 : 603 (11pages) (2008).*
Dempsey et al., Paired-End Sequence Mapping Detects Extensive Genomic Rearrangement and Translocation during Divergence of *Francisella tularensis* subsp. *tularensis* and *Francisella tularensis* subsp. *holarctica* Populations. Journal of Bacteriology 188 (16) :5904 (2006).*
Farrar et al., Construction and screening of BAC libraries made from *Brachypodium* genomic DNA. Nature Protocols 2(7) :1661(2007).*
Fullwood et al., Next-generation DNA sequencing of paired-end tags (PET) for transcriptome and genome analyses. Genome Research 19 : 521(2009).*
Green E., Strategies for the systematic sequencing of complex genomes. Nature Reviews/Genetics 2 :573 (2001).*
Harris et al., Single-molecule DNA sequencing of a viral genome. Science 320 :106 (2008).*
Margulies et al., Genome sequencing in microfabricated high-density picolitre reactors. Nature 437 :376 (2005).*
McKernan et al., Sequence and structural variation in a human genome uncovered by short-read, massively parallel ligation sequencing using two-base encoding. Genome Research 19 :1527 (2009).*
Ruan et al., Fusion transcripts and transcribed retrotransposed loci discovered through comprehensive transcriptome analysis using Paired-End diTags (PETs). Genome Research 17 : 828 (2007).*
Venter et al., A new strategy for genome sequencing. 381: 364 (1996).*
Yim et al., A BAC pooling strategy combined with PCR-based screenings in a large, highly repetitive genome enables integration of the maize genetic and physical maps. BMC Genomics 8 : 47 (12 pages) (2007).*
The International Search Report received in the parent application PCT/NL2010/050854, dated Apr. 14, 2011.
The International Search Report received in the related application NL 2004005, dated Jul. 12, 2010.
Klein P., et al., "A high-throughput AFLP-based method for constructing integrated genetic and physical maps: Progress toward a *Sorghum* Genome Map", Genome Research, 2000, vol. 10, No. 6, pp. 789-807.
Quiniou, et al., "A first generation BAC-based physical map of the channel catfish genome", BMC Genomics, 2007, vol. 8, No. 1. (XP021022345).

\* cited by examiner

*Primary Examiner* — Ethan C Whisenant
(74) *Attorney, Agent, or Firm* — Sunit Talapatra; Foley & Lardner LLP

(57) ABSTRACT

Method for de novo whole genome sequencing based on a (sequence-based) physical map of a DNA sample clone bank based on end-sequencing tagged adapter-ligated restriction fragments, in combination with sequencing adapter-ligated restriction fragments of the DNA sample wherein the recognition sequence of the restriction enzyme used in the generation of the physical map is identical to at least part of the recognition sequence of the restriction enzyme used in the generation of the DNA sample.

14 Claims, 7 Drawing Sheets

Fig 5
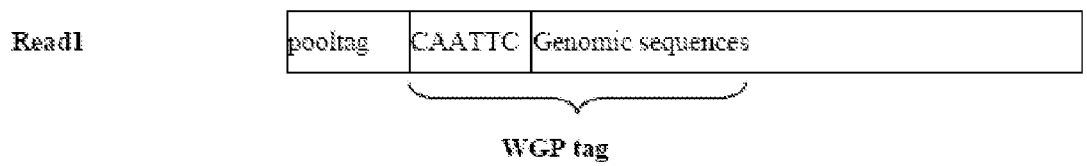
Fig 6A
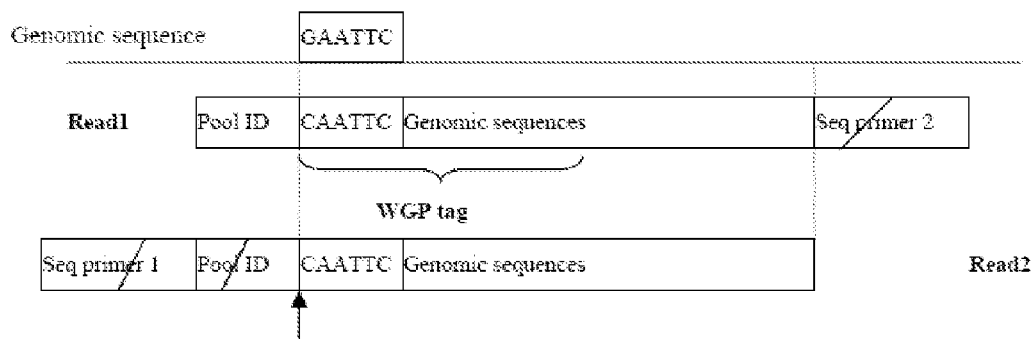
FG 6B
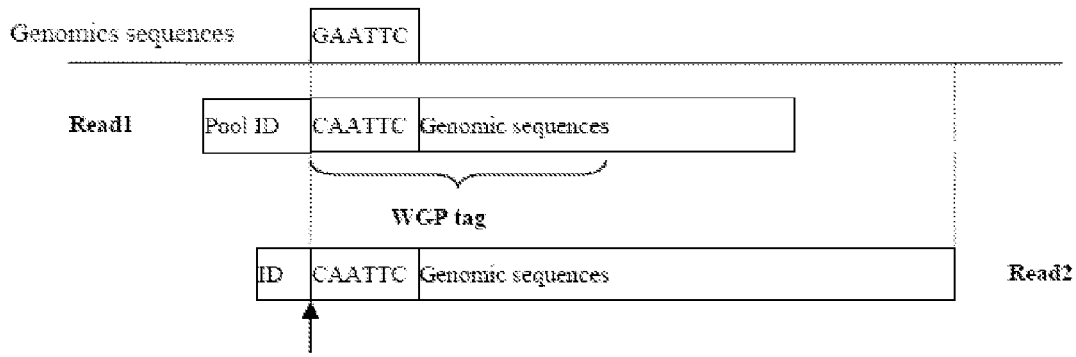

FIG 7

```
phrapcontig        GAATTCAGTGGAGGATTGTGGGGTGGGTTGGCGAGGACTCGGTTTTTTTCGGCGTCGGAG
Cap3Contig         GAATTCAGTGGAGGATTGTGGGGTGGGTTGGCGAGGACTCGGTTTTTTTCGGCGTCGGAG
pairedend_velvet   ------------------------------------------------------------
read2only_velvet   ------------------------------------------------------------ phrapcontig        AATAAACTTTCCGGCGAAGTTTCGCCGGCGATATTTACAGGGGTTTGTAATTTGGAGGTT
Cap3Contig         AATAAACTTTCCGGCGAAGTTTCGCCGGCGATATTTACAGGGGTTTGTAATTTGGAGGTT
pairedend_velvet   ------------------------------------------------------------
read2only_velvet   ------------------------------------------------------------ phrapcontig        TTGGACTTGTCAGAGAATGCGCTTTTCGGCGGAGCTCCGGCGGAGGTTTCTAATTGTGGG
Cap3Contig         TTGGACTTGTCAGAGAATGCGCTTTTCGGCGGAGCTCCGGCGGAGGTTTCTAATTGTGGG
pairedend_velvet   ---------------------------------------------TTCGAATTGTGGG
read2only_velvet   ---------------------------------------------TTCGAATTGTGGG phrapcontig        AATTTATCTTCTTGAATCTGTGGCGG-AACCAATTTTCTGCGAAGATTCCGCCTGAAAT
Cap3Contig         AATTTATCTTCTTGAATCTGTGGCGG-AACCAATTTTCTGCGAAGATTCCGCCTGAAAT
pairedend_velvet   AATTTGTCTTCTTGAATCTGTGGCGG-AACCAATTTTCTGCGAAGATTCCGCCGGAAAT
read2only_velvet   AATTTATCTTCTTGAATCTGTGGCGG-AACCAATTTTCTGCGAAGATTCCGCCGGAAAT phrapcontig        AGGAAGAATTTCGGCGTTTGCAGAATTTGTATCTAGGAAGGAACAAATTTCTCGGGAAAT
Cap3Contig         AGGAAGAATTTCGGCGTTTGCAGAATTTGTATCTAGGAAGGAACAAATTTCTCGGGAAAT
pairedend_velvet   AGGAAGAATTTCGGCGTTTGCAGAATTTGTATCTAGGAAAGAACAAATTTCTCGGGAAAT
read2only_velvet   AGGAAGAATTTCGGCGTTTGCAGAATTTGTATCTAGGAAAGAACAAATTTCTCGGGAAAT phrapcontig        TCCAGAATCCCTTTTGAATTTGAGCAATTGGTGTTTCTTGATTGAGCAAGAACAATTT
Cap3Contig         TCCAGAATCCCTTTTGAATTTGAGCAATTGGTGTTTCTTGATTGAGCAAGAACAATTT
pairedend_velvet   TCCAGAATCCCTTTTGAATTTGAGCAATTGGTGTTTCTTGATTGAGCAAGAACAATTT
read2only_velvet   TCCAGAATCCCTTTTGAATTTGAGCAATTGGTGTTTCTTGATTGAGCAAGAACAATTT phrapcontig        CGGAGGGGACATTCAAGAGATTTCGGAAGGTTTACACAGCTGAGATTCTTGTTCTTCA
Cap3Contig         CGGAGGGGACATTCAAGAGATTTCGGAAGGTTTACACAGCTGAGATTCTTGTTCTTCA
pairedend_velvet   CGGAGCGGACATTCAAGAGATTTCGGAAGGTTTACACAGCTGAGATTCTTGTTCTTCA
read2only_velvet   CGGAGCGGACATTCAAGAGATTTCGGAAGGTTTACACAGCTGAGATTCTTGTTCTTCA phrapcontig        TGGAAATTTTACACTGGAGGGATTCATTCTTCTGGGATTCTTAAGTTGCTAAGAGTTGC
Cap3Contig         TGGAAATTTTACACTGGAGGGATTCATTCTTCTGGGATTCTTAAGTTGCTAAGAGTTGC
pairedend_velvet   TGGAAATTTTACACTGGAGGGATTCATTCTTCTGGGATTCTTAAGTTGCCAAGAGTTGC
read2only_velvet   TGGAAATTTTACACTGGAGGGATTCATTCTTCTGGGATTCTTAAGTTGCCAAGAGTTGC phrapcontig        TCGTTTGGATTTGAGTTTCAAGAACTTTTCAGTTCCATTGCCTCTGGAAATCTCTGAAAT
Cap3Contig         TCGTTTGGATTTGAGTTTCAAGAACTTTTCAGTTCCATTGCCTCTGGAAATCTCTGAAAT
pairedend_velvet   TCGTTTGGATTTGAGTTTCAAGAACTTTTCAGTTCCATTGCCTCTGGAAATCTCTGAAAT
read2only_velvet   TCGTTTGGATTTGAGTTTCAAGAACTTTTCAGTTCCATTGCCTCTGGAAATCTCTGAAAT phrapcontig        GAAGAGCTTGGAGTTCTTGATTCTTGCATATAATCAGTTCAATGAAACATTCCATCAGA
Cap3Contig         GAAGAGCTTGGAGTTCTTGATTCTTGCATATAATCAGTTCAATGGA-------------
pairedend_velvet   GAAGAGCTTGGAGTTCTTGATTCTTGCATATAATCAGTTCAATGGAAACATTCCATCAGA
read2only_velvet   GAAGAGCTTGGAGTTCTTGATTCTTGCATATAATCAGTTCAATGGAAACATTCCATCAGA phrapcontig        ATATGGGAACTTGAAGAATCTTCAAGCTCTTGACCTTTCATTCAACAGCTTAAATGGGTC
Cap3Contig         ------------------------------------------------------------
pairedend_velvet   ATATGGGAACTTGAAGAATCTTCAAGCTCTTGACCTTTCATTCAACAGCTTAAATGGGTC
read2only_velvet   ATATGGGAACTTGAAGAATCTTCAAGCTCTTGACCTTTCATTCAACAGCTTAAATGGGTC phrapcontig        AATCCAAGAAGCT
```

FIG 8

```
Q         1 GAACAAAAAGAATAACATACAGCCGCATAACACACACGCTTTCAATCCTAGTATTTTTCT
            ||||||||||||||||||||||||||||||||||||||||||||||||||||||||||||
T     22056 GAACAAAAAGAATAACATACAGCCGCATAACACACACGCTTTCAATCCTAGTATTTTTCT

Q        61 TTTTCTTCGTCGCACAATACAAATGCACAAGGCAAATAAAAAGACCACACAAATAAGGAA
            ||||||||||||||||||||||||||||||||||||||||||||||||||||||||||||
T     22116 TTTTCTTCGTCGCACAATACAAATGCACAAGGCAAATAAAAAGACCACACAAATAAGGAA

Q       121 AGACCATCAACTGGCCATAAGGACCACCCACAACAATATGACCAAAGCAATAAGGAAAGT
            ||||||||||||||||||||||||||||||||||||||||||||||||||||||||||||
T     22176 AGACCATCAACTGGCCATAAGGACCACCCACAACAATATGACCAAAGCAATAAGGAAAGT

Q       181 TAAAGCATGGGAACAAAATAACAACGACTTTTTACTGCCAACCAAAAAGTAATTTATAAG
            ||||||||||||||||||||||||||||||||||||||||||||||||||||||||||||
T     22236 TAAAGCATGGGAACAAAATAACAACGACTTTTTACTGCCAACCAAAAAGTAATTTATAAG

Q       241 CACCTTTGAATAAGTTAACTATTCAATAATTTATACAAAATTAATTAACATCTATGATGA
            ||||||||||||||||||||||||||||||||||||||||||||||||||||||||||||
T     22296 CACCTTTGAATAAGTTAACTATTCAATAATTTATACAAAATTAATTAACATCTATGATGA

Q       301 ACTCGTAGGTTTATCAGCAACTGGAGTTTCATATTCAGATTCGAAAGGAAAGTTACACAC
            ||||||||||||||||||||||||||||||||||||||||||||||||||||||||||||
T     22356 ACTCGTAGGTTTATCAGCAACTGGAGTTTCATATTCAGATTCGAAAGGAAAGTTACACAC

Q       361 AGCATCCATTCACAAAAATGGTGAGATAATTGTAAGTGCAGGAGCCATTGGAAGTCCTCA
            ||||||||||||||||||||||||||||||||||||||||||||||||||||||||||||
T     22416 AGCATCCATTCACAAAAATGGTGAGATAATTGTAAGTGCAGGAGCCATTGGAAGTCCTCA

Q       421 ACTTCTCCTTCTAAGTGGAATTGGCCCGAAATCTCATCTTTCATCCTTAAAACTACCTGT
            ||||||||||||||||||||||||||||||||||||||||||||||||||||||||||||
T     22476 ACTTCTCCTTCTAAGTGGAATTGGCCCGAAATCTCATCTTTCATCCTTAAAACTACCTGT

Q       481 CGTTCTTCACCAACCTCACGTCGGACAGTTTATGACGGACAATCCCCGTTTCGGTACCAC
            ||||||||||||||||||||||||||||||||||||||||||||||||||||||||||||
T     22536 CGTTCTTCACCAACCTCACGTCGGACAGTTTATGACGGACAATCCCCGTTTCGGTACCAC

Q       541 CATTGTCCTTCCATTCCAATTACTTCCTTCAGCTGGAAAAGTTGTCGGAATTTTACAAGA
            ||||||||||||||||||||||||||||||||||||||||||||||||||||||||||||
T     22596 CATTGTCCTTCCATTCCAATTACTTCCTTCAGCTGGAAAAGTTGTCGGAATTTTACAAGA

Q       601 AAATATCTATATACAATCTTTCGCTGGCCCTTCAACATTTTTAGTTCCACCAGCTTTCAG
            ||||||||||||||||||||||||||||||||||||||||||||||||||||||||||||
T     22656 AAATATCTATATACAATCTTTCGCTGGCCCTTCAACATTTTTAGTTCCACCAGCTTTCAG

Q       661 CCTCCTTCCTCCTCAATCCACTTCCATCAACCCCACCTTAGCAAGTTTTGTTGGTAAATT
            ||||||||||||||||||||||||||||||||||||||||||||||||||||||||||||
T     22716 CCTCCTTCCTCCTCAATCCACTTCCATCAACCCCACCTTAGCAAGTTTTGTTGGTAAATT

Q       721 CTCTGATGTCAATTCTAAAGGGTGGCTTCATTTGAATTC
            |||||||||||||||||||||||||||||||||||||||
T     22776 CTCTGATGTCAATTCTAAAGGGTGGCTTCATTTGAATTC
```

RESTRICTION ENZYME BASED WHOLE GENOME SEQUENCING

CROSS-REFERENCE TO RELATED APPLICATION

This application is a national stage of PCT/NL2010/050854, filed on Dec. 16, 2010 under 35 U.S.C. §371, published in English and claims the benefit of U.S. Provisional Application No. 60/287,440, filed Dec. 17, 2009 and the Netherlands Patent Application 2004005, filed on Dec. 22, 2009, all which are incorporated herein by reference in entirety.

TECHNICAL FIELD OF THE INVENTION

The present invention relates to methods and strategies for the efficient generation of whole genome sequences or parts thereof using high throughput sequencing. The invention relates to large-scale nucleic acid sequencing and in particular to methods for sequencing the genome, or a part thereof, of an organism. The invention relates to improved strategies for determining the sequence of, preferably complex (i.e. large) genomes, based on the use of high throughput sequencing technologies.

BACKGROUND OF THE INVENTION

The goal of many sequencing projects is to determine, for the first time, the entire genome sequence of a target organism (de novo draft genome sequencing). Having a draft genome sequence at hand enables identification of useful genetic information of an organism, for instance for the identification of the origin of genetic variation between species or individuals of the same species. Hence, it is a general desire in the art to come to techniques that allow the de novo determination of the entire genome sequence of an individual, whether human, animal or plant at a reasonable cost and effort. This quest is typically indicated as the quest for the 1000$-genome, i.e. determining the entire genome sequence of an individual for a maximum of 1000$ (without considering currency fluctuations). However, in practice the 1000$ genome does not necessarily rely on de novo genome sequencing and assembly strategy but may also be based on a re-sequencing approach. In case of the latter, the re-sequenced genome will not be assembled de novo, but its DNA sequenced compared to (mapped onto) an existing reference genome sequence for the organism of interest. A re-sequencing approach is therefore technically less challenging and less costly. For sake of clarity, the focus of the current invention is on de novo genome sequencing strategies, capable to be applied to organisms for which a reference genome sequence is lacking.

Current efforts are varying, plentiful and rapidly increasing results are achieved. Nevertheless, the goal has not been achieved yet. It is still not economically feasible to sequence and assemble an entire genome in a straight forward fashion. There exists still a need in the art for improved de novo genome sequencing strategies. General requirements for such strategies are that they are cheaper, efficient in terms of computational power necessary to process data from sequence reads to an assembled draft genome, efficient in terms of the use of high throughput sequencing equipment to generate data of sufficient quality, i.e. the redundancy with which sequences need to be determined to create sufficiently accurate data etc.

WO03/027311 describes a clone-array pooled shotgun sequencing method (CAPPS). The method employs random sequence reads from differently pooled (BAC) clones. Based on the cross-assembly of the random reads a sequence contig can be generated from a plurality of clones and a map of the clones relative to the sequence can be generated. The publication describes, in more detail, the generation of a BAC library in a multidimensional pool, for example a two-dimensional format where each pool and row contain 148 BAC clones (148×148 format). Using CAPPS, BAC pools are sequenced to 4-5× coverage on average, which generates 8-10× coverage per BAC in case of the two-dimensional pool scheme. The contigs are made per BAC separately based on sequences that are unique to the BAC based on their occurrence in a single row and an single pool in case of a two-dimensional pooling scheme. Subsequently these BACs are assembled in a contig for the genome. The publication demonstrates the technology based on 5 BACs only and leaves the problem of data-processing untouched. One of the disadvantages of this technology is that the use of randomly sheared fragments requires an enormous amount of reads to cover a genome at a sequence redundancy level of 8 to 10 fold, making this method very laborious on larger scale. Furthermore it does not yield a sequence based physical BAC map.

US2007/0082358 describes a method of assembly of sequence information based on a clonally isolated and amplified library of single stranded genomic DNA to create whole genome shotgun sequence information combined with whole genome optical restriction mapping using a restriction enzyme for the creation of an ordered restriction map.

US2002/0182630 discloses a method on BAC contig mapping by comparison of subsequences. The method aims at avoiding the difficulties associated with repetitive sequences and the generation of contigs by the creation of bridges across repeat-rich regions.

Determining physical maps based on BACs can be based on sequencing BAC libraries (sequence-based physical mapping of BAC clones) using for instance the method described in WO2008/007951 from Keygene also indicated as 'whole genome profiling' or WGP. In brief, WGP relates to the generation of a physical map of at least part of a genome comprising the steps of generating an artificial chromosome library from a sample DNA, pooling the clones, digesting the pooled clones with restriction enzymes, ligating identifier-containing adapters, amplifying the identifier-containing adapter-ligated restriction fragments, correlating the amplicons to the clones and ordering the fragments to generate a contig to thereby create a physical map.

Despite all developments in high throughput sequencing, determining draft genome sequences with high accuracy is still considered expensive and laborious and fierce competition is present in the market. There hence remains a need to complement the currently existing methods to come to efficient and economic methods for the generation of draft genome sequences.

SUMMARY OF THE INVENTION

The present inventors have found novel and efficient strategies provide improvement of the existing methodologies based on the recent developments in sequencing technologies. The strategy is, in principle, based on a physical map from a clone bank using restriction fragments. Restriction fragments from clones or from genomic DNA, obtained by a restriction enzyme that contains the same recognition sequence as was used in the generation of the physical map, are used to generate further sequence information in a subsequent step using sequencing of fragmented restriction fragments, deconvolution (when using clones) and alignment to the physical map. The result is the generation of sequence reads that are linked to the restriction fragment, where the restriction fragment itself is linked to the physical map. Using this combined approach, the physical map as well as the draft genome sequence can be achieved through the combination of restriction fragment sequencing coupled with sequencing internal sequences of restriction fragments.

DEFINITIONS

As used herein, 'paired end sequencing' is a method that is based on high throughput sequencing, particular based on the platforms currently sold by Illumina and Roche. Illumina has released a hardware module (the PE Module) which can be installed in the existing sequencer as an upgrade, which allows sequencing of both ends of the template, thereby generating paired end reads. It is in particular preferred to use paired end sequencing, in particular using Solexa technology, in the methods according to the current invention. Examples of paired end sequencing are described for instance in US20060292611 and in publications from Roche (454 sequencing).

Sequencing: The term sequencing refers to determining the order of nucleotides (base sequences) in a nucleic acid sample, e.g. DNA or RNA. Many techniques are available such as Sanger sequencing and high-throughput sequencing technologies (also known as next-generation sequencing technologies) such as the GS FLX platform offered by Roche Applied Science, based on pyrosequencing.

Restriction enzyme: a restriction endonuclease or restriction enzyme is an enzyme that recognizes a specific nucleotide sequence (target site) in a double-stranded DNA molecule, and will cleave both strands of the DNA molecule at or near every target site, leaving a blunt or a staggered end.

A Type-IIs restriction endonuclease is an endonuclease that has a recognition sequence that is distant from the restriction site. In other words, Type IIs restriction endnucleases cleave outside of the recognition sequence to one side. Examples there of are NmeAlll (GCCGAG(21/19)) and FokI, AlwI, Mme I. There are Type IIs enzymes that cut outside the recognition sequence at both sides.

Frequent cutters and rare cutters: Restriction enzymes typically have recognition sequences that vary in number of nucleotides from 4 (such as MseI) to 6 (EcoRI) and even 8 (NotI). The restriction enzymes used can be frequent and rare cutters. The term 'frequent' in this respect is typically used in relation to the term 'rare'. Frequent cutting endonucleases (aka frequent cutters) are restriction endonucleases that have a relatively short recognition sequence. Frequent cutters typically have 4 or 5 nucleotides that they recognise and subsequently cut. Thus, a frequent cutter on average cuts a DNA sequence every 256-1024 nucleotides. Rare cutters are restriction endonucleases that have a relatively long recognition sequence. Rare cutters typically have 6 or more nucleotides that they recognise and subsequently cut. Thus, a rare 6-cutter on average cuts a DNA sequence every 4096 nucleotides, leading to longer fragments. It is observed again that the definition of frequent and rare is relative to each other, meaning that when a 4 bp restriction enzyme, such as MseI, is used in combination with a 5-cutter such as AvaII, AvaII is seen as the rare cutter and MseI as the frequent cutter.

Methylation sensitive restriction enzymes (MSRE). Restriction enzymes that are sensitive to the methylation status of a nucleotide in or near its recognition sequence. The presence or absence of a specific methylated nucleotide (usually Cytosine) is, next to the recognition sequence, decisive for the activity of the enzyme. NotI, SmaI, XmaI, MboI, BstBI, ClaI, MM, NaeI, NarI, PstI, PvuI, SadI, SaiI, HpaII, and HhaI are examples of MSREs Other useful MSREs are described, for example, in McClelland et al., Nucl. Acids Res. 22:3640-3659 (1994) or in technical materials available from commercial vendors such as New England Biolabs (Beverly, Mass.), Promega (Madison, Wis.), or Invitrogen (Carlsbad, Calif.).

Isoschizomers; Isoschizomers are pairs of restriction enzymes specific to the same recognition sequence and cut in the same location. For example, Sph I (GCATGˆC) and Bbu I (GCATGˆC) are isoschizomers of each other. The first enzyme to recognize and cut a given sequence is known as the prototype, all subsequent enzymes that recognize and cut that sequence are isoschizomers. An enzyme that recognizes the same sequence but cuts it differently is a neoschizomer. Isoschizomers are a specific type (subset) of neoschizomers. For example, Sma I (CCCˆGGG) and Xma I (CˆCCGGG) are neoschizomers (not isoschizomers) of each other.

Restriction fragments: the DNA molecules produced by digestion of DNA with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis or sequencing. Restriction fragments can be blunt ended or have an overhang. The overhang can be removed using a technique described as polishing. The term 'internal sequence' of a restriction fragment is typically used to indicate that the origin of the part of the restriction fragment resides in the sample genome, i.e. does not form part of an adapter. The internal sequence is directly derived from the sample genome, its sequence is hence part of the sequence of the genome under investigation. The term internal sequence is used to distinguish over adapters, remains of recognition sequence of restriction enzymes etc.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case, the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adapters: short double-stranded DNA molecules with a limited number of base pairs, e.g. about 10 to about 30 base pairs in length, which are designed such that they can be ligated to the ends of restriction fragments. Adapters are generally composed of two synthetic oligonucleotides that have nucleotide sequences which are partially complementary to each other. When mixing the two synthetic oligonucleotides in solution under appropriate conditions, they will anneal to each other forming a double-stranded structure. After annealing, one end of the adapter molecule is designed such that it is compatible with the end of a restriction fragment and can be ligated thereto; the other end of the adapter can be designed so that it cannot be ligated, but this need not be the case (double ligated adapters). Adapters can contain other functional features such as identifiers, recognition sequences for restriction enzymes, primer binding sections etc. When containing other functional features the length of the adapters may increase, but by combining functional features this may be controlled.

Adapter-ligated restriction fragments: restriction fragments that have been capped by adapters on one or both ends.

Primers: in general, the term primers refer to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

DNA amplification: the term DNA amplification will be typically used to denote the in vitro synthesis of double-stranded DNA molecules using PCR. It is noted that other amplification methods exist and they may be used in the present invention without departing from the gist.

Nucleic acid: a nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

Complexity reduction: the term complexity reduction is used to denote a method wherein the complexity of a nucleic acid sample, such as genomic DNA, is reduced by the generation or selection of a subset of the sample. This subset can be representative for the whole (i.e. complex) sample and is preferably a reproducible subset. Reproducible means in this context that when the same sample is reduced in complexity using the same method and experimental conditions, the same, or at least comparable, subset is obtained. The method used for complexity reduction may be any method for complexity reduction known in the art. Examples of methods for complexity reduction include for example AFLP® (Keygene N.V., the Netherlands; see e.g. EP 0 534 858), the methods described by Dong (see e.g. WO 03/012118, WO 00/24939), indexed linking (Unrau et al., 1994, Gene, 145:163-169), etc. The complexity reduction methods used in the present invention have in common that they are reproducible. Reproducible in the sense that when the same sample is reduced in complexity in the same manner, the same subset of the sample is obtained, as opposed to more random complexity reduction such as microdissection, random shearing, or the use of mRNA (cDNA) which represents a portion of the genome transcribed in a selected tissue and for its reproducibility is depending on the selection of tissue, time of isolation etc.

Identifier: a short sequence that can be added or inserted to an adapter or a primer or included in its sequence or otherwise used as label to provide a unique identifier (aka barcode or index). Such a sequence identifier (tag) can be a unique base sequence of varying but defined length, typically from 4-16 bp used for identifying a specific nucleic acid sample. For instance 4 bp tags allow 4(exp4)=256 different tags. Using such an identifier, the origin of a PCR sample can be determined upon further processing or fragments can be related to a clone. Also clones in a pool can be distinguished from one another using these sequence based identifiers. Thus, identifiers can be sample specific, pool specific, clone specific, amplicon specific etc. In the case of combining processed products originating from different nucleic acid samples, the different nucleic acid samples are generally identified using different identifiers. Identifiers preferably differ from each other by at least two base pairs and preferably do not contain two identical consecutive bases to prevent misreads. The identifier function can sometimes be combined with other functionalities such as adapters or primers and can be located at any convenient position.

Tagging: the term tagging refers to the addition of a sequence tag to a nucleic acid sample in order to be able to distinguish it from a second or further nucleic acid sample. Tagging can e.g. be performed by the addition of a sequence identifier during complexity reduction or by any other means known in the art such as a separate ligation step. Such a sequence identifier can e.g. be a unique base sequence of varying but defined length uniquely used for identifying a specific nucleic acid sample. Using nucleotide based tags, the origin of a sample, a clone or an amplified product can be determined upon further processing. In case of combining processed products originating from different nucleic acid samples, the different nucleic acid samples can be identified using different tags.

Tagged library: the term tagged library refers to a library of tagged nucleic acids.

Aligning: With the term "aligning" is meant the comparison of two or more nucleotide sequences based on the presence of short or long stretches of identical or similar nucleotides. Several methods for alignment of nucleotide sequences are known in the art, as will be further explained below.

Alignment: positioning of multiple sequences in a tabular presentation to maximize the possibility for obtaining regions of sequence identity across the various sequences in the alignment, e.g. by introducing gaps. Several methods for alignment of nucleotide sequences are known in the art, as will be further explained below.

The term "contig" is used in connection with DNA sequence analysis, and refers to assembled contiguous stretches of DNA derived from two or more DNA fragments having contiguous nucleotide sequences. Thus, a contig is a set of overlapping DNA fragments that provides a partial contiguous sequence of a genome. A "scaffold" is defined as a series of contigs that are in the correct order, but are not connected in one continuous sequence, i.e. contain gaps. Contig maps also represent the structure of contiguous regions of a genome by specifying overlap relationships among a set of clones. For example, the term "contigs" encompasses a series of cloning vectors which are ordered in such a way as to have each sequence overlap that of its neighbours. The linked clones can then be grouped into contigs, either manually or, preferably, using appropriate computer programs such as FPC, PHRAP, CAP3 etc.

Fragmentation: A technique used to fragment DNA into smaller fragments. Fragmentation can be enzymatic, chemical or physical. Random fragmentation is a technique that provides fragments with a length that is independent of their sequence. Typically, shearing or nebulisation are techniques that provide random fragments of DNA. Typically, the intensity or time of the random fragmentation is determinative for the average length of the fragments. Following fragmentation, a size selection can be performed to select the desired size range of the fragments Physical mapping describes techniques using molecular biology techniques such as hybridisation analysis, PCR and sequencing to examine DNA molecules directly in order to construct maps showing the positions of sequence features Genetic mapping is based on the use of genetic techniques such as pedigree analysis to construct maps showing the positions of sequence features on a genome Deconvolution is a term used to describe the identification of an individual in a library by detection of the presence of a known associated indicator (i.e. label or identifier) in one or more pools or subpools Amplicons: When DNA (fragments) are amplified (for instance by using PCR) the DNA strands resulting from the amplification can be indicated as amplicons.

Polishing: digesting DNA with restriction enzymes can result in blunt or staggered ends (i.e. contain an overhang or contain extended bases), depending on the enzyme. Staggered ends can be blunted (the overhang removed) in a process depicted as 'polishing'. Polishing is achieved using DNA polymerases like T4 polymerase, Klenow DNA polymerase (Costa et al., Nucleic acids Research, 1994)

BRIEF DESCRIPTION OF THE FIGURES

FIG. 5. Relationship between read1 and WGP tag.

FIG. 6a. Read1 contains (part of) the sequencing primer 2 and read2 contains (part of) the combination of pool ID and sequencing primer 1.

FIG. 6b. Read2 contains (part of) the pool ID.

FIG. 7. Illustrative Assembly results of phrap, Cap3 and Velvet for the WGP tag "GAATTCAGTGGAGGAT-TGTGGGGTGG" bin with 1506 paired end reads.

FIG. 8 Illustrative Result of a Blast analysis of a contig generated for WGP tag "GAATTCAAATGAAGCCAC-CCTTTAGA" (=query) against the melon genome sequence (=target)

DETAILED DESCRIPTION OF THE INVENTION

Figure 1:
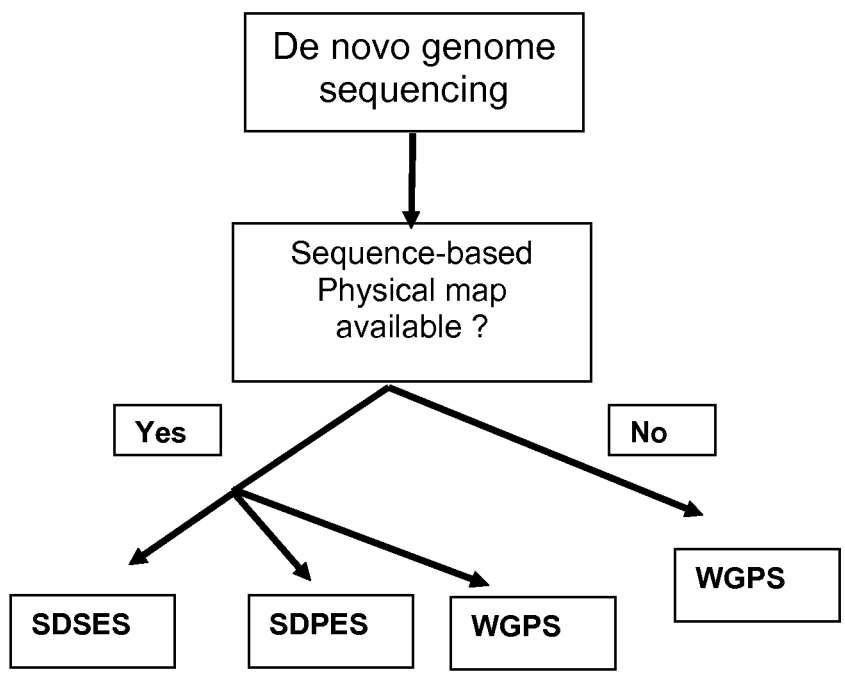
FIG. 1: Schematic representation of the sequencing strategies of the present invention.
Figure 2:
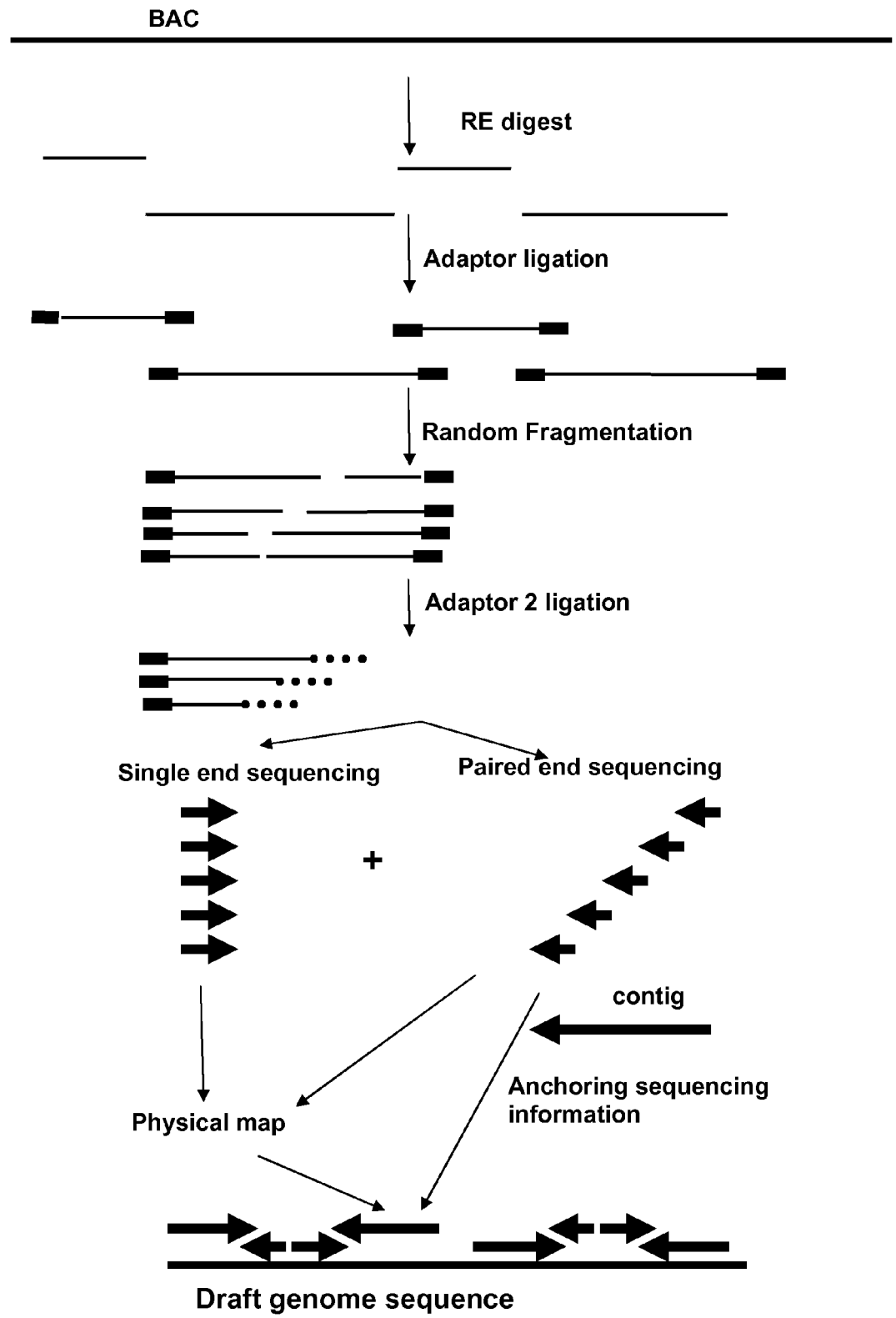
FIG. 2: Schematic representation of WGPS, Whole Genome Profile Sequencing
Figure 3:
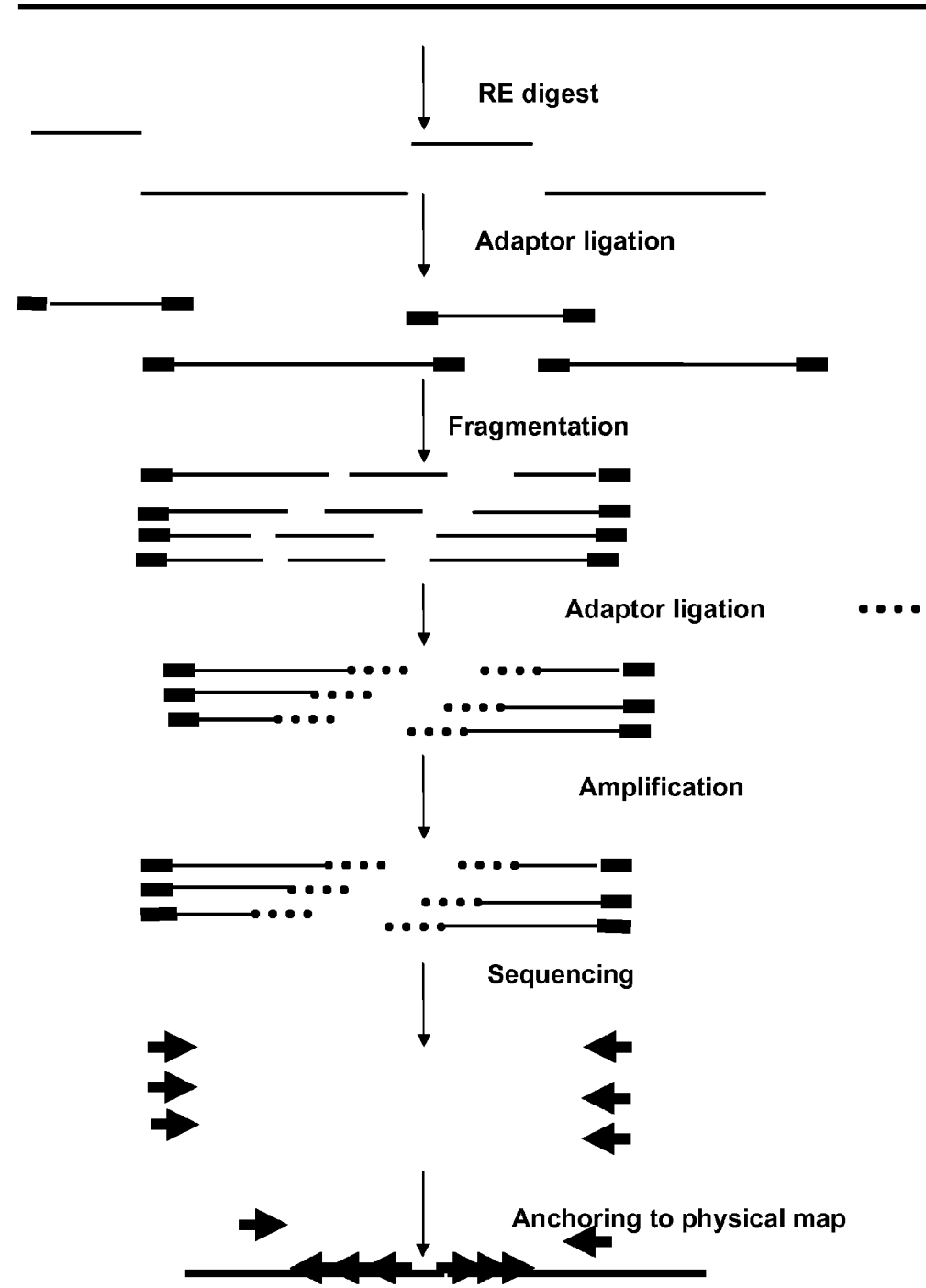
FIG. 3: Schematic representation of SDSES, Site-Directed Single End sequencing

In a first aspect, the invention relates to a method for the generation of sequence information from a DNA sample comprising
 a. providing a (sequence-based) physical map of a clone bank based on end-sequencing tagged adapter-ligated restriction fragments, wherein the restriction fragments have been generated using at least one restriction enzyme; and
 b. providing a submethod comprising the steps of
  i. providing adapter-ligated restriction fragments of the DNA sample
  ii. optionally, fragmenting the adapter-ligated restriction fragments
  iii. optionally, ligating adapters to the fragments of step (ii)
  iv. determining at least part of the sequence of the fragments of step (iii)
 c. combining the sequence information obtained in step (b) with the physical map of step (a);
 d. generating a draft genome sequence;
wherein the restriction fragments in step (b)(i) are generated with at least one restriction enzyme that contains a recognition sequence that is identical to at least part of the recognition sequence of the at least one restriction enzyme used in the generation of the physical map of step (a).

In the first step of the method, a physical map of a clone bank is provided by end-sequencing of adaptor-ligated restriction fragments. A physical map of a clone bank based on end-sequencing can be based on methods such as described in WO2008007951 'High throughput physical mapping', but also variants thereof can be used as exemplified below.

In applicants own WO2008007951, relating to high throughput physical mapping an efficient method is described for the generation of a physical map from a combination of restriction enzyme digestion of clones in a library, pooling, restriction enzyme digestion, adapter-ligation, (selective) amplification, high-throughput sequencing and deconvolution of the resulting sequences which results in BAC-clone specific sets that can be used to assemble physical maps. The assembly of the clones into contigs is based on the co-presence of terminal nucleotide sequence of the sequenced fragments, which can be used as sequence based anchor points for additional linkage of sequence data.

This technique is indicated as Whole Genome Profiling (WGP) and is KeyGene's recently developed proprietary approach for sequence-based physical mapping. Typically, a BAC library is constructed from a single (homozygous) individual and BAC clones are pooled in a multi-dimensional format. BAC pools are characterized by pool specific tags to allow assignment of sequences to individual BAC clones based on the coordinates in the multi-dimensional pool screening. DNA is extracted from each BAC pool and digested with one or more restriction enzymes, for instance EcoRI and MseI. The EcoRI ends of the restriction fragments are analyzed on a next-generation sequencer such as the Illumina Genome Analyzer and in this way these relative short (20-100 basepairs) sequenced fragments, called the WGP tags, can be assigned to individual BACs. In a next step, BACs can be assembled based on overlapping WGP tag patterns using a contiging software tool such as FPC (Soderlund et al.). Typically this leads to contigs of assembled BACs, with WGP tags every 2 to 4 kilobases, about 30-60 tags per BAC clone.

Compared to other physical mapping approaches such as SNaPshot mapping (for instance as used by Quiniou in BMC genomics 2007, 8, 1, 40), the WGP method is unique in providing sequence-based anchor points instead of fragment lengths for assembly of BAC contigs. Sequence-based anchors are more accurate and provide the basis for assembly of Whole Genome Shotgun data.

More in detail, physical mapping comprises the steps of:
 (a) providing an artificial chromosome (e.g. BAC, YAC) clone bank wherein each artificial chromosome clone contains DNA from a sample genome;
 (b) pooling the clones from the artificial chromosome library into pools;
 (c) providing a set of fragments for each pool using restriction enzymes;
 (d) ligating adapters to the fragments;
 (e) determining the sequence of at least part of the adapter and part of the fragment;

(f) assigning the fragments to the corresponding clones;

(g) ordering the clones into clone-contigs thereby generating a physical map of the sample genome.

In step (a) of the method an artificial clone bank is provided. The library can be a Bacterial Artificial Chromosome library (BAC) or based on yeast (YAC). Other libraries such as based on fosmids, cosmids, PAC, TAC or MAC are also possible. Preferred is a BAC library. The library is preferably of a high quality and preferably is a high insert size genomic library. This means that the individual BAC contains a relative large insert of the genomic DNA under investigation (typically>100 kbp). The size of the preferred large insert is species-dependent. Throughout this application, reference can be made to BACs as examples of artificial chromosomes. However, it is noted that the present invention is not limited thereto and that other artificial chromosomes can be used without departing from the gist of the invention. Preferably the libraries contain at least five genome equivalents, more preferably at least 7, most preferably at least 8. Particularly preferred is at least 10. The higher the number of genome equivalents in the library, the more comprehensive and reliable the resulting contigs and physical map will be.

In step (b), the individual clones in the library are pooled to form pools containing a multitude of artificial chromosomes or clones. The pooling may be the simple combination of a number of individual clones into one sample (for example, 100 clones into 10 pools, each containing 10 clones), but also more elaborate pooling strategies may be used. The distribution of the clones over the pools is preferably such that each clone is present in at least two or more of the pools. Preferably, the pools contain from 10 to 10000 clones per pool, preferably from 100 to 1000, more preferably from 250 to 750. It is observed that the number of clones per pool can vary widely, and this variation is related to, for instance, the size of the genome under investigation. Typically, the maximum size of a pool or a sub-pool is governed by the ability to uniquely identify a clone in a pool by a set of identifiers. A typical range for a genome equivalent in a pool is in the order of 0.2-0.3, and this may again vary per genome. The pools are generated based on pooling strategies well known in the art. The skilled man is capable selecting the optimal pooling strategy based on factors such as genome size etc. The resulting pooling strategy will depend on the circumstances, and examples thereof are plate pooling, N-dimensional pooling such as 2D-pooling, 3D-pooling, 6D-pooling or complex pooling. To facilitate handling of large numbers of pools, the pools may, on their turn, be combined in super-pools (i.e. super-pools are pools of pools of clones) or divided into sub-pools. Other examples of pooling strategies and their deconvolution (i.e. the correct identification of the individual clone in a library by detection of the presence of a known associated indicator (i.e. label or identifier) of the clone in one or more pools or subpools) are for instance described in U.S. Pat. No. 6,975,943 or in Klein et al. in Genome Research, (2000), 10, 798-807. The pooling strategy is preferably such that every clone in the library is distributed in such over the pools that a unique combination of pools is made for every clone. The result thereof is that a certain combination of (sub)pools uniquely identifies a clone.

In step (c) of the method, the pools are digested with restriction endonucleases to yield restriction fragments. Each pool is, preferably separately, subjected to an endonuclease digest. Each pool is preferably treated with the same (combination of) endonuclease(s) or those having the same recognition sequence. In principle, any restriction endonuclease can be used. Restriction endonucleases may be frequent cutters (4 or 5 cutters, such as MseI or AvaI) or rare cutters (6 and more cutters such as EcoRI, HindIII). Typically, restriction endonucleases are selected such that restriction fragments are obtained that are, on average, present in an amount or have a certain length distribution that is adequate for the subsequent steps. In certain embodiments, two or more restriction endonucleases can be used and in certain embodiments, combinations of rare and frequent cutters can be used. For large genomes the use of, for instance, three or more restriction endonucleases can be used advantageously to reduce complexity of the genome.

To one or both ends of the restriction fragments, adapters are ligated in step (d) to provide for adapter-ligated restriction fragments. Typically, adapters are synthetic oligonucleotides as defined herein elsewhere. The adapters used in the present invention preferably contain an identifier section, in essence as defined herein elsewhere, to provide for 'tagged adapters'. In certain embodiments, the adapter contains a pool-specific identifier, i.e. for each pool, an adapter containing a unique identifier is used that unequivocally indicates the pool. In certain embodiments, the adapter contains a degenerate identifier section which is used in combination with a primer containing a pool-specific identifier.

In certain embodiments, the adapter-ligated restriction fragments can be combined in larger groups, in particular when the adapters contain a pool-specific identifier. This combination in larger groups may aid in reducing the number of parallel amplifications of each set of adapter-ligated restriction fragments obtained from a pool.

Alternatively, the adapters that are ligated do not contain an identifier or a degenerate identifier section. The adapter-ligated fragments are subsequently amplified using primers that contain identifiers (tags), for instance at their 5'end. The result is that amplified, tagged adapter-ligated fragments are obtained. In this embodiment, the adapters can be the same for a plurality (or all) of the pools and the amplification using tagged primers creates the distinction between the pools that can later be used in the deconvolution. Either way, a set of tagged adapter-ligated fragments is obtained that are linked to the pool from which they originate by the presence of the tag.

The tagged adapter-ligated fragment can be amplified. The amplification may serve to reduce the complexity or to increase the amount the DNA available for analysis. The amplification can be performed using a set of primers that are at least partly complementary to the adapters and or the tags/identifiers. This amplification may be independently from the amplification described herein above that introduces the tags into the adapters, but it may be in one combined step. In certain embodiments, the amplification may serve several purposes at a time, i.e. reduce complexity, increase DNA amount and introduce tags in the adapter-ligated fragments in the pools. In certain embodiments, the amplification may be in separate stages using different primers, for instance first increasing the amount of available DNA using adaptor-directed primers, then the introduction of tags by using primers containing tags, followed by complexity reduction using primers that can select amongst adaptor-ligated fragments, for instance using randomly selective nucleotide at the 3'end or by using (pooled) primers that amplify certain tagged adapters.

In certain embodiments, the adapter-ligated fragments can be combined in larger groups, in particular when the adapters contain a pool-specific identifier. This combination in larger groups may aid in reducing the number of parallel amplifications of each set of adapter-ligated restriction fragments obtained from a pool.

The adapter-ligated fragments can be amplified using a set of primers of which at least one primer amplifies the pool-specific identifier at the position of the pool-specific or degenerate identifier in the adapter. The primer may contain (part of) the identifier, but the primer may also be complementary to a section of the adapter that is located outside the tag, i.e. downstream in the adapter. Amplification then also amplifies the tag.

In step (e) part of the sequence of the tagged adapter-ligated fragment is determined. The tagged adapter-ligated fragments are subjected to sequencing, preferably high throughput sequencing as described herein elsewhere. During sequencing, at least part of the nucleotide sequence of the (amplified) tagged adapter-ligated fragment is determined. Preferably at least the sequence of the pool-specific identifier and part of the fragment (i.e. derived from the sample genome) of the (amplified) tagged adapter-ligated fragment is determined. Preferably, a sequence of at least 10 nucleotides of the fragment is determined. In certain embodiments, at least 15, 20, 25, 30 or 35 nucleotides of the fragment (i.e. derived from the sample genome) are determined. The number of nucleotides that are to be determined minimally will be, again, genome—as well as sequencing platform dependent. For instance, in plants more repetitive sequences are present, hence longer sequences (25-75 nucleotides) are to be determined for a contig of comparable quality. For instance, in silico calculations on the known genome sequence of *Arabidopsis* have shown that, when including a 6 bp restriction site in the sequencing step, about 20 bp per fragment needs to be determined in order to ensure that the majority (>80%) of sequences are unique in the genome. It is possible to determine the sequence of the entire fragment, but this is not an absolute necessity for contig building of a BAC clone.

In the sequencing step, to provide for maximum coverage of all fragments and increased accuracy, the sequence library may be sequenced with an average redundancy level (aka oversampling rate) of at least 5. This means that, on average, the sequence is determined of at least 5 amplicons obtained from the amplification of one specific adapter-ligated fragment. In other words: each fragment is (statistically) sequenced on average at least five times. Increased redundancy is preferred as it improves the fraction of fragments that are sampled in each pool and the accuracy of these sequences, so preferably the redundancy level is at least 7, more preferably a least 10. Increased average sequencing redundancy levels are used to compensate for a phenomenon that is known as 'sampling variation', i.e. random statistical fluctuation in sampling subsets from a large "population". In addition, a higher average sequencing redundancy level alleviates possible differences in the abundance of amplified fragments which result from differences in their amplification rates caused by length variation between fragments and differences in sequence composition.

It is preferred that the sequencing is performed using high-throughput sequencing methods, such as the pyrosequencing-based methods disclosed in WO 03/004690, WO 03/054142, WO 2004/069849, WO 2004/070005, WO 2004/070007, and WO 2005/003375, by Seo et al. (2004) Proc. Natl. Acad. Sci. USA 101:5488-93, and technologies of Helicos, Illumina, US Genomics, etcetera, which are herein incorporated by reference.

In the following step (f), the (partly) sequenced (amplified) tagged adapter-ligated fragments are correlated or assigned to the corresponding clone, typically in silico by means of computerized methods. The (amplified) tagged adapter-ligated fragments are selected that contain identical sections of nucleotides in the restriction fragment-derived part. Subsequently the different pool-specific identifiers (tags) are identified that are present in those (amplified) tagged adapter-ligated fragments. The combination of the different pool-specific identifiers and hence the sequence of the restriction fragment can be uniquely assigned to a specific clone (a process described earlier as 'deconvolution'). For example, in the case of a 3D pooling strategy (X,Y,Z), each pool in the library is uniquely addressed by a combination of 3 pool-specific identifiers with the same restriction fragment-derived section. In other words: a restriction fragment-derived section originating from a clone will be tagged with 3 different identifiers. Unique restriction fragment-derived sections, when observed in combination with the 3 identifiers can be assigned to a single BAC clone. This can be repeated for each (amplified) tagged adapter-ligated fragment that contains other unique sections of nucleotides in the restriction fragment-derived part.

After assigning the fragments to the corresponding clones in step (f), the clones are combined and ordered into clone contigs in step (g) of the method. The grouping and ordering can be performed by fingerprint contiging software for this purpose such as FPC software (Soderlund et al (1997) FPC: a system for building contigs from restriction fingerprinted clones. Comput. Appl. Biosci., 13:523-535) essentially as described herein elsewhere. The alignment of the clones into contigs and the corresponding order of WGP tags generates a physical map of the sample genome.

In the submethod of the invention, adapter-ligated restriction fragments are provided. As a starting material for the generation of the adapter ligated restriction fragments, a sample genome can be used, or a part of a sample genome can be used, or a collection of BAC clones, varying from one singular BAC clone to an entire library of BAC clones, so also subsets of a BAC library are possible, comprising one or more BAC clones. When BAC clones are used, pools of BAC clones may be used, using similar or identical pooling and deconvolution strategies as described herein elsewhere. In the submethod, the DNA sample is preferably from the same individual, line or source as the DNA sample used to generate the physical map in step (a). Alternatively, the DNA sample in the submethod may be from a different source, such as a relative from the individual, a member of the same line etc.

The starting material is fragmented into restriction fragments by digesting with at least one restriction enzyme that contains a recognition sequence that is identical to at least part of the recognition sequence of the at least one restriction enzyme used in the generation of the physical map.

In certain embodiments the same restriction enzymes are used for the generation of the physical map and for the generation of the restriction fragments for the second step. In alternative embodiments they may have the same recognition sequence or contain at least part of the recognition sequence of the restriction enzyme used to create the physical map. In certain embodiments, the recognition sequence of the restriction enzyme encompasses the recognition sequence of the restriction enzyme used in the creation of the physical map. For example, the restriction enzyme PacI has as recognition sequence TTAATTAA whereas restriction enzyme MseI has a recognition sequence TTAA which recognition sequence as a whole is present in the first restriction enzyme.

In certain embodiments, the restriction enzymes employed in the two methods may be isoschizomers or neoschizomers. Combinations of restriction enzymes are also possible to influence the number of restriction fragments or to reduce complexity, for instance via selective amplification.

To the restriction fragments of the second substep ((b)(i)), adapters can be ligated. Typically, adapters are synthetic oligonucleotides as defined herein elsewhere. The adapters used in the present invention preferably contain an identifier section, in essence as defined herein elsewhere to provide for 'tagged adapters' When the adapter is ligated it is preferred not to restore the recognition sequence of the restriction endonuclease. Typically, when one restriction enzyme is used in the fragmentation, the adapter will be ligated to both ends of the fragment. The adapters used may in certain embodiments be biotinylated. The adapters may be labelled with an affinity label such as biotin to allow for later on (streptavidine-based) selection of the affinity-labelled adapters. In particular, first affinity-labelled adapters are ligated to obtained affinity-labelled adapter-ligated restriction fragments. When two or more restriction enzymes are used, two or more different adapters may be used which may or may not be independently labelled with an affinity label. The adapter may further contain an identifier substantially as described herein elsewhere to allow for pooling and deconvolution strategies.

The adapters can be the same as used in the generation of the physical map and may contain identifiers, which may the same as used in the generation of the physical map. In certain embodiments, the adapters may contain a recognition sequence for a restriction enzyme, preferably a type IIs enzyme.

In certain embodiments relating to the presence of a Type IIs recognition sequence in the adapter, this step may be followed by a circularisation step followed by digestion with a type IIs enzyme. To the IIs-digested site an adapter can be ligated and the thus adapter-ligated fragment can be subjected to a fragmentation.

The adapter-ligated fragments can now be fragmented, resulting in fragmented adapter-ligated fragments. Typically, this may result in DNA fragments that on one end contain an adapter and on the other side end with nucleotides derived from the sample nucleic acid sequence ('naked ends'). This second fragmentation step can be performed with another, (non-selective) restriction enzyme or by random fragmentation such as shearing or nebulisation.

To these 'naked ends', which in certain embodiments may be polished and may have undergone A-addition ('A-tailing), adapters are ligated. These adapters may be the same or different as the adapters used in step (iii) and may be tagged.

In a subsequent step, these adapter-ligated naked ends are now sequenced, i.e. at least part of the sequence of the fragments is determined. Preferably, the adaptor-ligated ends are end-sequenced, i.e. one or both ends of the sequence are determined containing part of the adaptor and part of the internal fragment. This results in a set of sequence fragments. These sequence fragments can be correlated, via the adapters and identifiers to restriction sites on the physical map and can hence be correlated to the physical map. For each set of fragments that can be correlated to a restriction site on the physical map, these set of fragments can be anchored to the map and they may also be contiged to further add sequence information to a specific location (WGP tag) of the physical map.

Using this method, it is possible to determine WGP-tags on a physical map and subsequently add sequence data to these WGP tags, thereby further completing the physical map and generating a draft genome sequence of the sample, or at least a part thereof.

The method of the present invention is embodied in three different embodiments that all share the above common concept. The three embodiments will now be discussed herein below.

In a first embodiment, dubbed WGPS, the physical map is not yet available and is determined side by side with the desired further sequence information which is needed to be added to the physical map, anchored to the WGP tags. In two other embodiments, SDSES and SDPES, respectively, the physical map is already available, and the sequence data generated serves to further complement the existing physical map. In certain embodiments where the physical map is already available, WGPS may nevertheless be used to generate additional sequence information. Depending on the embodiments, there may be a preference for certain sequencing techniques and the (length of the) sequence reads that are produced thereby. This is schematically depicted in FIG. 1.

WGPS (Whole Genome Profile Sequencing)

Thus, in a first variant of the method of the invention, the physical map is determined together (simultaneous, parallel or subsequently) with the fragment sequences.

The physical map is determined as outlined herein above and the same variations and embodiments apply. For the sake of clarity, they are repeated here in relation to WGPS.

In addition thereto, the adapter-ligated restriction fragments of the BAC clones are subject to further fragmentation, adapter ligation and sequencing as outlined herein below.

The whole method, including the generation of the physical map, comprises the steps of:
  (a) providing a clone bank comprising a plurality of clones wherein each clone contains DNA from a sample genome (or part of the sample genome);
  (b) pooling the clones from the clone bank into pools;
  (c) providing fragments for each pool using at least one restriction enzyme;
  (d) ligating first adapters to the fragments;
  (e) fragmenting the adapter-ligated restriction fragments of step (d) to provide fragmented adapter-ligated restriction fragments and, optionally, polish the random fragment ends;
  (f) ligating second adapters to the (polished) fragmented restriction fragments to provide adapter-ligated fragmented restriction fragments, containing first and second adapters;
  (g) optionally, amplifying the adapter-ligated fragmented restriction fragments of step (f) with a first and a second primer thereby generating amplicons;
  (i) determining the sequence of at least part of the first adapter and/or part of the fragment adjacent to the first adapter and/or of at least part of the second adapter and/or part of the fragment adjacent to the second adapter;
  (j) assigning the fragments to the corresponding clones based on the sequenced part of the first adapter and/or part of the fragment adjacent to the first adapter and/or of part of the second adapter and/or part of the fragment adjacent to the second adapter;
  (k) ordering the clones into clone-contigs thereby generating a physical map of the sample genome;
  (l) assigning the fragment sequences of at least part of the second adapter and/or part of the fragment adjacent to the second adapter to the corresponding clone;
  (m) anchoring the fragment sequences of step (h) to the physical map;
  (n) generating a draft genome sequence.

In one embodiment, the method further comprises a step of assembling the sequences derived from the first adapter and part of the fragment adjacent to the first adaptor and the sequences derived from the second adaptor and part of the fragment adjacent to the second adaptor into a contig that is linked to the physical map. In a further step, this particular contig may be anchored to the physical map. This 'binning' approach creates a sub-assembly step that may be efficient when larger data sets are handled.

The advantages of this embodiment of the method of the invention reside inter alia in the combined use of paired end sequence data of fragments of restriction fragments. One of the sequence reads is directly related to the fragment sequences of the restriction fragment to build the physical map, the fragment sequences of the randomly fragmented ends are random, yet physically linked to the fragment used to build the physical map.

The different steps of the method are discussed in more detail herein below.

In the WGPS embodiment, both adapters may contain identifiers, which may be used to correlate the fragment with the clone.

The (tagged) restriction fragments of step (d) are fragmented. Fragmentation of the tagged restriction fragments provides fragmented tagged adapter ligated restriction fragments. The obtained fragments may contain an adapter on the 3' or 5' end of the fragment, or not at all, if the fragment is the middle section of a double fragmented tagged restriction fragments. Fragmentation is preferably random and preferably via shearing or nebulisation or by using sequence composition-independent nucleases. Typically, a fragment thus contains an adapter-ligated end and a random end. It is possible to select a set of fragments in a desired size range using common knowledge technology therefore. The fragments may be polished at the random ends. In certain alternative embodiments, the polishing step is followed by the addition of one or more specific nucleotides to provide for an anchoring and orientation point of the second adaptor which is then of a staggered design.

To the random ends, (second) adapters are ligated. When the random ends are polished, the adapters are blunt ended such that they ligate to each random end present. Sometimes these are indicated as second adapter (with the adapters ligated to the restriction fragments as indicated in step (e) then being seen as the first adapters.

The resulting sequences, i.e. the adapter-ligated fragmented tagged restriction fragments may be amplified using two primers, a first and a second primer. The first primer is directed against the, optionally tagged, restriction fragment end and may contain sections that are at least complementary to part of the (first) adapter that amplifies at least the identifier (or the degenerate identifier section). The second primer may be directed against (is complementary to) at least part of the, optionally tagged, adapter ligated to the random end of the restriction fragment. The amplification, preferably using PCR, results in amplified fragmented tagged restriction fragments (amplicons). Depending on the number of different amplicons available, amplicons may be combined from various experiments in a set of amplicons for instance to accommodate the capacity of the sequencing platform used. The amplicons may be combined in certain embodiments, in a set of combined amplicons or a so-called sequence library.

In step (i) of the method, the sequences of one or both ends of the adaptor-ligated fragments or amplicons can be determined, preferably using paired end sequencing. With sequencing, at least the optional sequence of the identifier located in the first and/or second adapter and/or part of the internal sequence of the fragment located adjacent to the first and/or second adapter are determined. Sequencing in the method of the present invention is typically based on high throughput sequencing such as pyrosequencing on Roche (454) and Illumina platforms disclosed herein.

The adaptor-ligated fragments or amplicons are subjected to sequencing, preferably high throughput sequencing as described herein. During sequencing, at least part of the nucleotide sequence of the amplicons is determined. Preferably, a sequence of at least 10 nucleotides of the fragment is determined, preferably from each side. In certain embodiments, at least 20, 25 or 30 nucleotides of the fragment are determined. The number of nucleotides that are to be determined minimally will be, again, genome—as well as sequencing platform dependent. For instance, in plants more repetitive sequences are present, hence longer sequences (25-75 nucleotides) are to be determined for a contig of comparable quality. Current platforms can handle significantly longer reads (100-800 nt).

As mentioned before, the sequencing of the present invention is preferably performed using 'paired end sequencing'.

Paired end sequencing provides also part of the internal sequence of the fragment adjacent to the second adapter. By performing paired end sequencing, the two sequences are determined simultaneously. Based on the identifier and the part of the internal sequence, the sequences can be grouped into sets that originate from the same restriction fragment. The sequence information from the random ends provides information on the composition of the internal sequence of the restriction fragment. By grouping all information obtained from a restriction fragment together and creating a contig of the sequences obtained from the random ends and the information obtained from the first adapter and adjacent fragment sequences may provide a draft sequence of most of the (if not the entire) restriction fragment.

In step (j) the fragments are associated with the corresponding clones. Typically, the deconvolution to generate the physical map of the genome is based on the presence of identifiers in the adapters that correlate the fragment to the pools and hence, based on the pooling strategy to the corresponding clone. Thus, the fragments are assigned to the corresponding clones based on the sequenced part of the first adapter and/or part of the fragment adjacent to the first adapter and/or of part of the second adapter and/or part of the fragment adjacent to the second adapter. For instance, a physical map is available based on two restriction enzymes, for instance EcoRI/MseI, then a WGPS embodiment using HindIII may provide additional information that can be linked to the EcoRI/MseI based physical map.

In step (k) of the method the physical map is generated by ordering the clones using commonly known software for this purpose.

In step (l) of the method, the fragments sequences obtained form the second adapter and/or the fragment adjacent thereto are coupled to the corresponding clone such that a group of fragment sequences is obtained that are linked (in step j) to a certain clone via a restriction fragment sequencing in step (i). This is based on (j), i.e. the fact that the sequence of at least part of the second adapter and/or part of the fragments adjacent to the second adapter is derived from the same fragment based on paired-end sequencing. The thus obtained sequence can be anchored to the physical map and the draft genome generated.

In certain embodiments when a physical map is already available, WGPS may nevertheless be used to generate additional sequence information that can be linked the to initial physical map, for instance by using different restriction enzymes for the WGPS.

SDSES (Site Directed Single End Sequencing)

In a further embodiment of the method of the present invention, the submethod of step (b) of the method of the invention comprises the steps of
  (a) fragmentation of a target DNA (genomic DNA or artificial chromosome DNA) with at least one restriction endonuclease to obtain restriction fragments;

(b) ligation of a first adapter to the ends of the restriction fragments to obtain first adapter-ligated restriction fragments;

(c) random fragmentation of the first adapter-ligated restriction fragments to obtain randomly fragmented first adapter-ligated restriction fragments;

(d) optionally, selection of the fragmented adapter-ligated restriction fragments that contain an adapter;

(e) ligation of a second adapter to the fragmented ends of the first adapter-ligated restriction fragments;

(f) optionally, amplification using a primer directed against the adapter of step (b) and an (affinity-labelled) primer directed against the second adapter of step (e) to obtain (affinity-labelled) amplified fragments;

(g) optionally, selection of the (affinity-labelled) amplified fragments obtained in step (f) based on the presence of the second adapter;

(h) determination of the sequence of at least part of the first adapter and/or part of the sequence of the fragment adjacent to the first adaptor and/or of at least part of the second adapter and/or part of the sequence of the fragment adjacent to the second adaptor.

In step (a) of the method, a target DNA is provided. The target DNA can be obtained from any source, whether genomic or clone-based. Isolation from DNA can be achieved by any means in the art such as disclosed for instance by Sambrook et al. (Sambrook and Russell (2001) "Molecular Cloning: A Laboratory Manual (3rd edition), Cold Spring Harbor Laboratory, Cold Spring Harbor Laboratory Press). The sample DNA can be from any species, in particular from human, plant or animal origin. It is preferred to take the same DNA sample as was used in the generation of the physical map, but other samples as outlined herein above may also be used (i.e. from a related individual, a line etc.)

In the embodiment directed to clone DNA, an clone bank is provided. This may be the same clone bank used to generate the physical map. The clone bank (or library) can be a Bacterial Artificial Chromosome library (BAC) or based on yeast (YAC). Other libraries such as based on fosmids, cosmids, PAC, TAC or MAC are also possible. Preferred is a BAC library. The library is preferably of a high quality and preferably is a high insert size genomic library. This means that the individual BAC contains a relative large insert of the genomic DNA under investigation (typically>125 kbp). The size of the preferred large insert is species-dependent. Throughout this application reference can be made to BACs as examples of artificial chromosomes. However, it is noted that the present invention is not limited thereto and that other artificial chromosomes can be used without departing from the gist of the invention. The individual clones in the library may be pooled to form pools, containing a multitude of artificial chromosomes or clones. The pooling may be the simple combination of a number of individual clones into one sample (for example, 100 clones into 10 pools, each containing 10 clones), but also more elaborate pooling strategies may be used. The distribution of the clones over the pools is preferably such that each clone is present in at least two or more of the pools. Preferably, the pools contain from 10 to 10000 clones per pool, preferably from 100 to 1000, more preferably from 250 to 750. It is observed that the number of clones per pool can vary widely, and this variation is related to, for instance, the size of the genome under investigation. Typically, the maximum size of a pool or a sub-pool is governed by the ability to uniquely identify a clone in a pool by a set of identifiers. A typical range for a genome equivalent in a pool is in the order of 0.2-0.3, and this may again vary per genome. The pools are generated based on pooling strategies well known in the art. The skilled man is capable selecting the optimal pooling strategy based on factors such as genome size etc. The resulting pooling strategy will depend on the circumstances, and examples thereof are plate pooling, N-dimensional pooling such as 2D-pooling, 3D-pooling, 6D-pooling or complex pooling. To facilitate handling of large numbers of pools, the pools may, on their turn, be combined in super-pools (i.e. super-pools are pools of pools of clones) or divided into sub-pools. Other examples of pooling strategies and their deconvolution (i.e. the correct identification of the individual clone in a library by detection of the presence of a known associated indicator (i.e. label or identifier) of the clone in one or more pools or subpools) are for instance described in U.S. Pat. No. 6,975,943 or in Klein et al. in Genome Research, (2000), 10, 798-807. The pooling strategy is preferably such that every clone in the library is distributed in such over the pools that a unique combination of pools is made for every clone. The result thereof is that a certain combination of (sub)pools uniquely identifies a clone.

It is possible to use only a part of a genome, but that is not essential, as the present invention also provides for methods to accommodate genomes of any size, for instance through the creation of reproducible subsets via reproducible complexity reduction such as for instance selective amplification based on AFLP (EP534858). Thus, typically, the present method uses the entire genome. Alternatively, clone banks, or parts thereof can be used.

The target DNA is restricted with a restriction enzyme to yield restriction fragments. The target DNA can be restricted with at least one restriction enzyme. In certain embodiments, two or more enzymes can be used to generate restriction fragments of the desired length and distribution. In certain embodiments, it may be advantageous to use three restriction endonucleases to arrive at restriction fragments of the desired length distribution. The restriction enzymes may cut blunt or staggered (i.e. create an overhang) with a preference for staggered in view of subsequent adapter-ligation).

The enzymes and the combination of enzymes are preferably selected such that, on average, the length of the fragments is about 400-1000 bp, depending on, for instance, the sequencing platform used. There is a preference for rare cutters such as EcoRI.

To the restriction fragments of the second substep, adapters can be ligated. Typical adapters are synthetic oligonucleotides as defined herein elsewhere and they may contain identifiers and affinity labels etc.

In step (c) of the method, the adapter-ligated restriction fragments are randomly fragmented. Suitable and preferred techniques for random fragmentation are known as nebulisation or shearing or uses another, non-selective restriction enzyme.

Other techniques that provide for a controllable fragmentation of DNA are also suitable. Fragmentation of adapter-ligated restriction fragments will result in fragments carrying adapters on one end, on the other end as well as intermediate fragments that at both end are the result of a random fragmentation. The fragmented set may be subjected to the selection of a size range using common procedures.

The fragmented adapter-ligated restriction fragments may now be now selected in step (d), preferably using an affinity label, to separate them from the fragments remaining after the random fragmentation that do not carry an adapter or an affinity label, such as the fragments that are at both ends derived from a random fragmentation process (carry random ends'). Preferably, the combination biotin-streptavidine is used in the selection but other affinity-ligand combinations can be used as well, as well as carriers containing probes that hybridize to the adapters.

To the random ends of the selected adapter-ligated restriction fragments, a second adapter can be ligated in step (e). Prior to ligation of the second adapter, the random ends, i.e. the ends caused by the random fragmentation step, may be polished, i.e. overhanging nucleotides may be removed (blunted). The second adapter can be blunt ended. In certain alternative embodiments, the polishing step is followed by the addition of one or more specific nucleotides to provide for an anchoring and orientation point of the second adaptor which is then of a staggered design.

The adapter-ligated set may now be amplified in step (f) from a pair of suitable primers leading to amplified fragments (amplicons). The amplification is performed with a first primer that may be directed against at least part of the nucleotides of the first adapter (i.e. the adapter of step (b)). The second primer in the amplification is directed against (at least part of) the second adapter (i.e. of step (e). This first and/or second primer may be affinity labelled to obtain affinity labelled amplification products for a later selection step. The affinity label may be biotin, but it may also be different from the affinity label used in certain embodiments of step (b). For instance instead of biotin labelling it is also possible to use nucleotide-based affinity labels and base the selection step on hybridisation to a dipstick carrying oligonucleotides complementary that are complementary to the nucleotide based affinity labels to capture the fragments.

The resulting (optionally affinity-labelled) amplified fragments can be selected in the following step (step (g)) using the methods such as previously described, for instance using a carrier carrying streptavidine.

In step (h) of the method, the fragments can now be sequenced, for instance using high throughput sequencing technology based on pyrosequencing, essentially as described herein elsewhere. The sequence of at least part of the first adapter and part of the sequence of the fragment adjacent to the first adaptor are determined. In an alternative embodiment, the sequence of at least part of the second adapter and part of the sequence of the fragment adjacent to the second adaptor are determined. The sequenced fragments can be assembled into a contig and subsequently linked to the physical map or the sequence information can be directly anchored to the physical map, based on sequence identity.

The contigs, all starting with a sequence identical to the recognition site of the restriction enzymes used can be linked to the physical map which was generated using a restriction enzyme with an identical recognition sequence. Linking can be established by searching for the sequence of the WGP tag of the physical map in the sequences of the contigs that are adjacent to the restriction enzyme sequence. When a unique hit is found, the contig sequence can be linked to the physical map. In certain cases, the contigs will also comprise restriction enzyme sites at its end which indicates that the complete intermediate sequence has been determined.

In one aspect of the invention SDSES can also be applied as such for the generation of sequence information of a target DNA. Thus the present invention also relates to a method for the generation of sequence information of a target DNA comprising the steps of (a) fragmentation of a target DNA (genomic DNA or artificial chromosome DNA) with at least one restriction endonuclease to obtain restriction fragments;
(b) ligation of a first adapter to the ends of the restriction fragments to obtain first adapter-ligated restriction fragments;
(c) random fragmentation of the first adapter-ligated restriction fragments to obtain randomly fragmented first adapter-ligated restriction fragments;
(d) optionally, selection of the fragmented adapter-ligated restriction fragments that contain an adapter;
(e) ligation of a second adapter to the fragmented ends of the first adapter-ligated restriction fragments;
(f) optionally, amplification using a primer directed against the adapter of step (b) and an (affinity-labelled) primer directed against the second adapter of step (e) to obtain (affinity-labelled) amplified fragments;
(g) optionally, selection of the (affinity-labelled) amplified fragments obtained in step (f) based on the presence of the second adapter;
(h) determination of the sequence of at least part of the first adapter and/or part of the sequence of the fragment adjacent to the first adaptor and/or of at least part of the second adapter and/or part of the sequence of the fragment adjacent to the second adaptor.

SDPES (Site Directed Paired End Sequencing)

In a further embodiment of the method of the present invention, the submethod of step (b) of the method of the invention comprises the steps of (a) restriction enzyme digestion of target DNA to obtain restriction fragments;
(b) ligation of an IIs-adapter that contains a recognition sequence for a Type-IIs restriction endonuclease to provide IIs-adapter-ligated restriction fragments;
(c) fragmentation of the IIs-adapter-ligated restriction fragments to obtain fragmented IIs-adapter-ligated restriction fragments;
(d) circularisation of the fragmented IIs-adapter-ligated restriction fragments to obtain circularised products;
(e) Type-IIs restriction enzyme digestion of circularised products to provide Type-IIs digested fragments;
(f) ligation of a first adapter to the Type-IIs digested fragments to provide adapter-ligated Type-IIs digested fragments;
(g) fragmentation of the first adapter-ligated Type-IIs digested fragments;
(h) ligation of a second adapter to the first adapter-ligated Type-IIs digested fragments to provide first and second adapter-ligated Type-IIs digested fragments;
(i) determining the sequence of at least part of the fragments and/or adapters.

In step (a) of the method, a target DNA is provided. The target DNA can be obtained from any source, whether genomic or clone-based. Isolation of DNA can be achieved by any means in the art such as disclosed for instance by Sambrook et al. (Sambrook and Russell (2001) "Molecular Cloning: A Laboratory Manual (3rd edition), Cold Spring Harbor Laboratory, Cold Spring Harbor Laboratory Press). The sample DNA can be from any species, in particular from human, plant or animal origin. It is preferred to take the same DNA sample as was used in the generation of the physical map, but other samples as outlined herein above may also be used (i.e. from a related individual, a line etc.)

In the embodiment directed to clone DNA, an artificial clone bank is provided. This may be the same clone bank used to generate the physical map. The artificial clone bank (or library) can be a Bacterial Artificial Chromosome library (BAC) or based on yeast (YAC). Other libraries such as based on fosmids, cosmids, PAC, TAC or MAC are also possible. Preferred is a BAC library. The library is preferably of a high quality and preferably is a high insert size genomic library. This means that the individual BAC contains a relative large insert of the genomic DNA under investigation (typically>125 kbp). The size of the preferred large insert is species-dependent. Throughout this application reference can be made to BACs as examples of artificial chromosomes. However, it is noted that the present invention is not limited thereto and that other artificial chromosomes can be used without departing from the gist of the invention. The individual clones in the library may be pooled to form pools, containing a multitude of artificial chromosomes or clones. The pooling may be the simple combination of a number of individual clones into one sample (for example, 100 clones into 10 pools, each containing 10 clones), but also more elaborate pooling strategies may be used. The distribution of the clones over the pools is preferably such that each clone is present in at least two or more of the pools. Preferably, the pools contain from 10 to 10000 clones per pool, preferably from 100 to 1000, more preferably from 250 to 750. It is observed that the number of clones per pool can vary widely, and this variation is related to, for instance, the size of the genome under investigation. Typically, the maximum size of a pool or a sub-pool is governed by the ability to uniquely identify a clone in a pool by a set of identifiers. A typical range for a genome equivalent in a pool is in the order of 0.2-0.3, and this may again vary per genome. The pools are generated based on pooling strategies well known in the art. The skilled man is capable selecting the optimal pooling strategy based on factors such as genome size etc. The resulting pooling strategy will depend on the circumstances, and examples thereof are plate pooling, N-dimensional pooling such as 2D-pooling, 3D-pooling, 6D-pooling or complex pooling. To facilitate handling of large numbers of pools, the pools may, on their turn, be combined in super-pools (i.e. super-pools are pools of pools of clones) or divided into sub-pools. Other examples of pooling strategies and their deconvolution (i.e. the correct identification of the individual clone in a library by detection of the presence of a known associated indicator (i.e. label or identifier) of the clone in one or more pools or subpools) are for instance described in U.S. Pat. No. 6,975,943 or in Klein et al. in Genome Research, (2000), 10, 798-807. The pooling strategy is preferably such that every clone in the library is distributed in such over the pools that a unique combination of pools is made for every clone. The result thereof is that a certain combination of (sub)pools uniquely identifies a clone.

It is possible to use only a part of a genome, but that is not necessary as the present invention also provides for methods to accommodate genomes of any size, for instance through the creation of reproducible subsets via reproducible complexity reduction such as for instance selective amplification based on AFLP (EP534858). Thus typically, the present method uses the entire genome.

The target DNA is restricted with a restriction enzyme to yield restriction fragments. The target DNA can be restricted with at least one restriction enzyme. In certain embodiments, two or more enzymes can be used to generate restriction fragments of the desired length and distribution. In certain embodiments, it may be advantageously to use three restriction endonucleases to arrive at restriction fragments of the desired length distribution. The restriction enzymes may cut blunt or staggered (i.e. create an overhang) with a preference for staggered in view of subsequent adapter-ligation).

The enzymes and the combination of enzymes are preferably selected such that, on average, the length of the fragments is about 50-800 bp, depending on the readlength of the sequencing platform. There is a preference for rare cutters such as EcoRI.

In step (b) of the method, an adapter (indicated herein as the IIs-adaptor) is ligated to the restriction fragments obtained form step (a). The adapter contains a recognition sequence for a type IIs-restriction endonuclease to yield IIs-adapter-ligated restriction fragments. The IIs-adapter may contain an identifier, for instance in the case of pooled clone DNA.

In step (c) of the method, the IIs-adaptor-ligated fragments are randomly fragmented. The random fragmentation can be performed using common methods such as nebulisation, shearing or sequence composition-independent nucleases. Fragmentation can be performed to obtain fragments in a desired size range, which may depend on the sequencing platform used later on in the method. The obtained fragments may be subject to an intermediate size selection step. Where desired, the obtained fragments may be polished to obtain blunt ended fragment ends.

In step (d) of the method, the fragmented IIs-adapter-ligated restriction fragments are circularised to obtain circular products which can subsequently be cut (in step (e)) with the Type-IIs restriction endonuclease to yield Type-IIs digested fragments. To the Type-IIs digested fragments a first adapter is ligated in step (f). The first adapter is preferably ligated to the remains of the Type-IIs restriction site to provide for first adapter-ligated Type-IIs digested fragments. In step (g) of the method, the first adapter-ligated Type-IIs digested fragments are then again fragmented to yield a set of fragments of an useable size (typically about 150-800 bp, depending on the platform used).

In step (h) of the method, subsequent ligation of a second adapter results in first and second adapter-ligated Type-IIs digested fragments, i.e. a Type IIs digested fragment having a first or a second adapter ligated at each end, respectively. The first and/or second adapters may contain (different) identifiers. The first and second adapter-ligated Type-IIs digested fragments can now be sequenced and/or amplified using high throughput sequencing technology such as emulsion PCR or cluster amplification.

At least part of the sequence of the fragment is determined in the direction from the first adapter to the second adaptor or vice versa. Preferably, the sequence of the fragment is determined using paired-end sequencing as outlined herein elsewhere.

The obtained sequence information can be linked to the physical map. In one aspect of the invention SDPES can also be applied as such for the generation of sequence information of a target DNA. Thus the present invention also relates to a method for the generation of sequence information of a target DNA comprising the steps of
  (a) restriction enzyme digestion of target DNA to obtain restriction fragments;
  (b) ligation of an IIs-adapter that contains a recognition sequence for a Type-IIs restriction endonuclease to provide IIs-adapter-ligated restriction fragments;
  (c) fragmentation of the IIs-adapter-ligated restriction fragments to obtain fragmented IIs-adapter-ligated restriction fragments;
  (d) circularisation of the fragmented IIs-adapter-ligated restriction fragments to obtain circularised products;
  (e) Type-IIs restriction enzyme digestion of circularised products to provide Type-IIs digested fragments;
  (f) ligation of a first adapter to the Type-IIs digested fragments to provide adapter-ligated Type-IIs digested fragments;
  (g) fragmentation of the first adapter-ligated Type-IIs digested fragments;
  (h) ligation of a second adapter to the first adapter-ligated Type-IIs digested fragments to provide first and second adapter-ligated Type-IIs digested fragments;
  (i) determining the sequence of at least part of the fragments and/or adapters.

EXAMPLES

WGPS Example

A Melon BAC library superpool 24 was provided together with WGP data of superpool 24 to demonstrate successful WGPS on BAC pools through assembly of GA paired end reads linked to enzyme sites.

1. Wetlab Approach

The approach contains the following steps:

Digestion of the (individual) BAC pool DNAs using a single enzyme (EcoRI).

Ligation of pool specific EcoRI compatible adaptors which contain the P5 amplification, sequence primer 1 and a pool specific identifier sequence.

(Optional pooling of the RL products from super pools which will be sequenced in a single lane of e.g. the Illumine Genome Analyzer. This up to the maximum of different pool specific identifiers used in the previous ligation step)

Fragmentation of the adaptor ligated products into products with a size range of 100-1000 bp.

Fragmented adaptor ligated restriction fragments are end polished and a single A-nt is added to the fragmented ends.

To remove fragments that are too small, Ampure purification is performed with a sample:beads ratio of 1:1.8. This would remove fragments below 100 nt.

An adaptor containing a 3'-T overhang is ligated which contains the P7 amplification and the sequence primer 2 sequence.

To remove any remaining adaptors Ampure purification is performed using a sample to beads ratio of 1:1.3.

A fill-in reaction is performed to generate fully double stranded fragments through the filling in of the partially single stranded adaptors. Alternatively an amplification using P5 and P7 primers can be performed.

The final sample is purified using a Qiagen PCR purification column

The concentration is measured using the Nanodrop and the size distribution of the fragments is determined through analysis on the Agilent BioAnalyzer.

The generated libraries are sequenced using the Illumina Genome Analyzer II using a paired end 36 nt sequencing protocol.

The obtained sequencing data is processed using the standard Illumina Software pipeline v1.6.

Processed sequence data is exported and used as input for the WGP pipeline and for the assembly of the paired end reads.

2. Bioinformatics Approach 2.1 Deconvolution for Physical Map Generation

After processing of the data the average # reads per tag in a pool was ~450. This was approximately 7× higher than in normal WGP. Using this large dataset 9039 tags could be deconvoluted using the standard WGP pipeline. In the regular WGP data set 13571 tags were deconvoluted in the BACs pools used. Approximately 71% of the 9039 deconvoluted tags were also present in the regular WGP data set. Lower deconvolution is allocated to the extreme deep sequencing and a lower quality sequencing run. Both increase the number of reads containing errors which raises the number of tags that obtain multiple coordinates and are therefore not deconvoluted. The deconvoluted tags are to be used to generate a WGP map which will be used to position the contigs generated and selected in 2.2 step 5.

2.2 Assembly Paired End Data into Contigs

The approach includes six steps.

Step 1 trims pool tags from read1 of paired end reads. This because pool tags are used for deconvolution in the WGP process and not for assembly. This step also includes recovery of the modified restriction enzyme site from CAATTC to GAATTC. From the read1 generated ~85% started with the expected restriction enzyme site, after removal of the pool tags. Step 1b is to pool the reads based upon their BAC/pool tags. This will enable local assembly of the reads when clustering is performed on the pooled tags. This is an alternative (more fragmented) approach than mentioned in step 2.

Step 2 clusters paired end reads according to the corresponding WGPtag of read1. FIG. 5 indicates the relationship between WGPtag and read1. Step 1b might be added in order not to have problems assembling reads from repetitive regions in step 4.

Step 3 trims for each cluster the paired end reads containing artifact fragments, which is shown in FIGS. 6a and b. In the case of FIG. 6a, both read1 and read2 are trimmed for containing artifacts. Read1 is trimmed for containing part of the GAII sequence primer 2 and read2 is trimmed for containing the pool ID and part of the GAII sequence primer 1. The shared fragment sequence between read1 and read2 should be kept (between dashlines of read1 and read2, in FIG. 6a). FIG. 6b shows another example in which only read2 contains artifacts, part of pool tag.

Step 4 assembles the trimmed data set per cluster using the software tools phrap and/or cap3.

Step 5 picks up the assembled largest contigs from all clusters and performs statistic analysis. Pooling the paired end reads based upon their BAC IDs reduces the creation of multiple contigs. The current option assembles all repetitive regions having an identical WGP tag. In the current example only a single pool set of the 2D pooled melon BAC library was used, which minimized the presence of repetitive WGP tags. Using this approach on data from a complete BAC library would not give the maximum benefits of local assemblies. The approach as mentioned in Step 1b would circumvent assembly of repetitive regions.

Step 6 blasts these contigs against a (melon) draft genome, if available, for QC purposes.

Step 7 positions the contigs (step 5) on the WGP map generated in 2.1

Step 8 assembles the positioned (overlapping) contigs of step 7 into longer contigs. This would result in a draft genome sequence based on a physical map. This step might be performed before step 7, but this might result in incorrect assemblies due to repetitive sequences. Effectively this step is local assembly of local assemblies.

A few programs can be used to assemble GAII paired end reads per cluster. Tools evaluated were Velvet, Soapdenovo, ABySS, cap3 and phrap. Both Cap3 and phrap which are traditional assembly programs for Sanger reads, assembled the GAII reads per cluster very well. In the study, the settings for cap3 used were "-o 40 -p 80 -y 6" and distances between paired end reads were set to between 0 and 800 nt. Phrap does not take paired end distance and only treats these reads as shotgun reads. The settings for phrap used in this study were "-vector_bound 0 -forcelevel 1 -minscore 12 -minmatch 10 -indexwordsize 8". These settings were also used in a Nature paper entitled "Parallel, tag-directed assembly of locally derived short sequence reads" (Hiatt et al, 2010).

Figure 4:
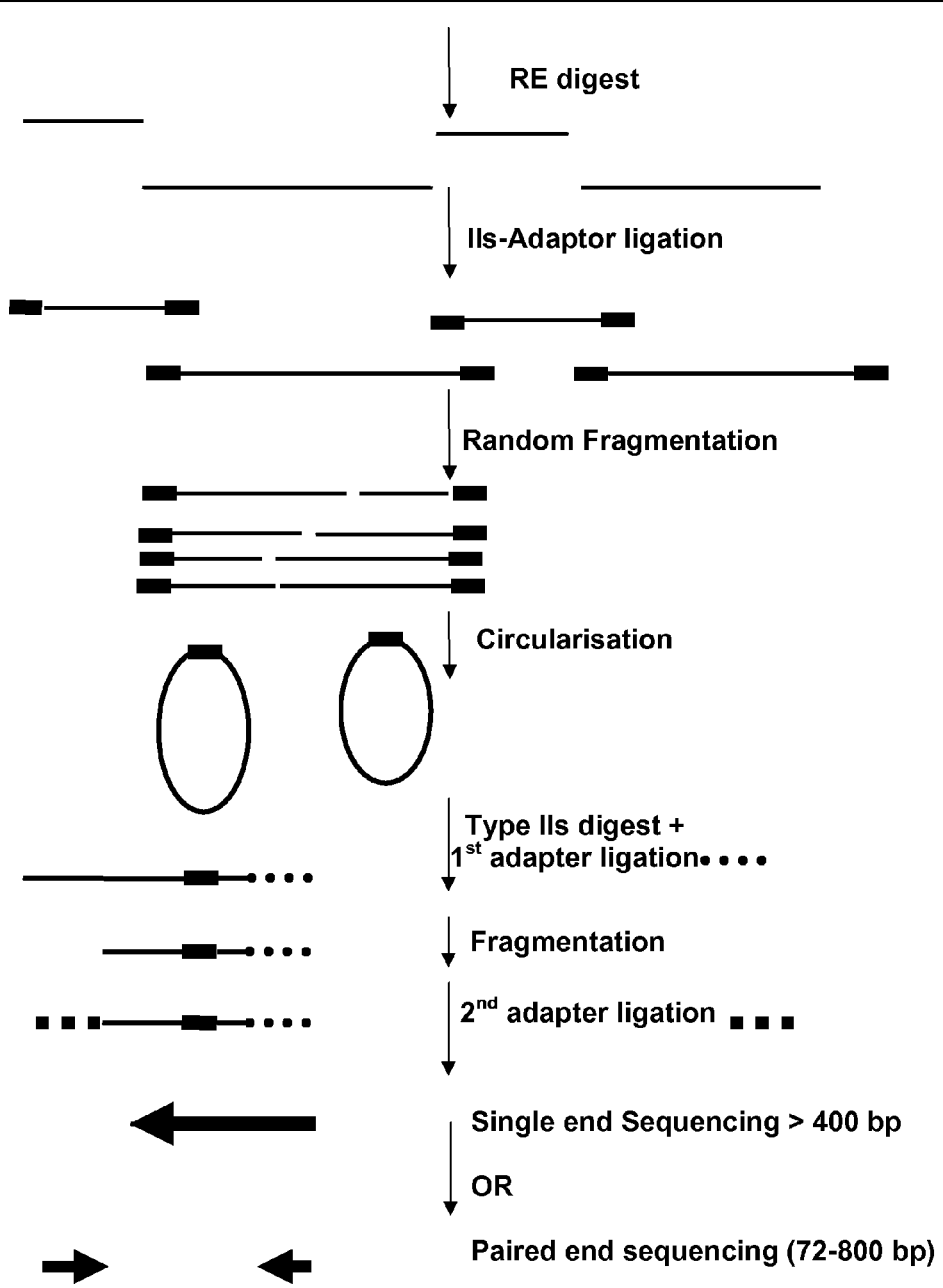
FIG. 4: Schematic representation of SDPES Site-Directed Paired End Sequencing.

FIG. 4 shows the assembly results for one cluster using Cap3, phrap or Velvet. Cap3 and Phrap generated fragments near the enzyme site, while Velvet missed that part in both paired end reads and read2 only due to sequence redundancy on that region.

Comparing Cap3 to others showed that Cap3 missed the end part because it trimmed off 3' side "low" quality region. This property in CAP3 is designed for Sanger read assemblies. Therefore, phrap performed the best and is the preferred assembler for this approach.

3 Results

From the sequence data generated in step 2.2 9039 tags were deconvoluted to identify a single BAC. Of these tags, 71% was also found in the original WGP tag list for the pools used. All reads generated in step 2.2 were binned based on their first read after which an assembly was performed on each bin individually. With the Phrap software the assembly resulted in a total of 15938 contigs of which 14905 (=94%) started with the expected restriction enzyme site. The average length of the contigs generated was ~545 nt. To check the quality of the assembled contigs, a subset was blasted against a melon genome sequence which was generated using a random sequencing approach. A result of the BLAST analysis is shown in FIG. 8. The figure shows that the generated WGPS contig (760 nt) has a 100% match with a genome sequence contig. This match was the only hit with a high significance.

SDSES example

A Melon BAC library superpool 24 was provided together with WGP data of superpool 24 to demonstrate SDSES on genomic DNA of melon through linking enzyme linked sequence information to the WGP map of melon.

Wetlab Approach

The approach contains the following steps:

1—Nuclear DNA is isolated to decrease the amount of sequence data obtained from chloroplast and mitochondria. This is an optional step but would increase the useable output.

2—Digestion of melon genomic DNA using a single enzyme (EcoRI). This enzyme is preferably the same enzyme as used in the generation of the WGP map. If a different enzyme is to be used, it should (preferably) recognize the same nucleotides (GAATTC) as the enzyme used in WGP.

3—Ligation of enzyme (EcoRI) compatible adaptors which contain the amplification and sequence primer.

4—Fragmentation of the adaptor ligated products into products with a size range of at least 400 bp with a maximum of 1000 bp. The lower fragment length may vary but should at least be higher than the sequencing read length that can be obtained.

Fragmentation can be performed using nebulization or sonication (Covaris).

5—Size distribution and concentration of the purified fragments is determined through analysis the Agilent Bioanalyzer using a high sensitivity DNA chip (size distribution) and a nanodrop measurement (concentration)

6—Small fragments (<400 nt) are removed through size selection using the AMpure procedure as used in the library preparation protocol for GS-FLX sequencing.

After size selection the concentration of the sample is measured on the nanodrop 7—Purified fragments are end polished.

8—The polished products are (optionally) purified through capturing the fragments on streptavidin coated magnetic beads. This is possible when the ligated EcoRI adaptor used contains a 5'-biotin modification.

9—To prevent concatenation a single A is added to the polished random ends of the fragments.

10—A T-shaped adaptor is ligated which contains the amplification and sequence primer 2 sequences.

11—An amplification is performed to generate fully double stranded fragments and amplified sample, which contains a biotin modification at the 5'end of one DNA strand.

12—The amplification products are bound to magnetic streptavidin coated beads (Dynal) using the protocol as mentioned above.

13—The unlabeled strand of fragments is eluted from the beads and used for sequencing using a (next generation) sequencing technology Sequencing The above prepared sample is sequenced using the Roche GS-FLX titanium sequencer. Raw sequence data is processed using the General Sequencing Signal processing tools. This will trim sequence reads on quality and the presence of the adaptor sequences used in the library preparation. After filtering there were 930,618 reads with an average read length of 380 bp remaining. This corresponds to 354 Mbp of sequence information. Fasta (fna) and corresponding quality (.qual) files are extracted from the raw sequence file(s) (.sff). The fasta, quality and raw sequence files are processed using the bioinformatics processing steps mentioned below.

Bioinformatics Processing

Removal of all reads not starting with the (modified) restriction enzyme recognition site In this example EcoRI is used which means that reads not starting with CAATTC are removed. If an alternative enzyme is used, filtering will have to be performed using a different recognition site.

All reads containing internal recognition sites for the enzyme used for the preparation of the sequencing library are removed. These reads might be chimeric. In this example all reads containing internal GAATTC are removed.

In the remaining reads the modified restriction enzyme (EcoRI) site (CAATTC) is restored. The restore (or adjusted trimming point adjusted) will facilitate integration of the generated contigs with WGS and/or WGP data.

The results of the sequence data processing are given in table 2.

TABLE 2

Sequence read processing overview

| | # | % |
|---|---|---|
| Past filter reads | 930483 | 100.0% |
| Reads with NO internal EcoRI (=GAATTC) site | 922401 | 99.1% |
| Reads with internal EcoRI (=GAATTC) site | 8082 | 0.9% |
| Reads starting with modified EcoRI (=CAATTC) site | 893811 | 96.9% |
| Reads NOT starting with modified EcoRI (=CAATTC) site | 28590 | 3.1% |
| Reads with restored EcoRI (=GAATTC) site | 893811 | 96.1% |

The processed sequence reads are assembled using the CAP3 software using the following settings -p 97 (overlap identity cutoff) and -y 6 (clipping range). Other options are used with their default values. The results of this assembly are given in table 3.

Assembled contigs are screened for presence of internal restriction sites for the enzyme used in the sequencing library preparation, i.e. EcoRI in this example. Contigs with internal sites are likely assembled reads based upon their internal sequences and not on the sequence flanking the restriction enzyme site, which at the start of the sequence read.

TABLE 3

Cap3 assembly results overview

|  | # | % |
|---|---|---|
| Contigs | 93038 | 100.0% |
| Singletons | 366965 | 41.0% |
|  |  | (of input) |
| Contigs starting with EcoRI (=GAATTC) site | 92799 | 99.7% |
| Contigs NOT starting with EcoRI (=GAATTC) site | 239 | 0.3% |
| Contigs EcoRI-EcoRI | 4881 | 5.2% |
| Contigs containing internal EcoRI site | 276 | 0.3% |
| Contigs starting with EcoRI (=GAATTC) site and no internal EcoRI site | 92509 | 99.4% |
| EcoRI-EcoRI and no internal EcoRI site | 4850 | 5.2% |

Contigs with internal restriction sites are removed from the selection.

Contigs without internal restriction sites are combined with the unassembled reads into a new fasta file The fasta file (containing the contigs and singletons of the previous step) is reassembled using Cap3 and the settings as mentioned above. Results of the reassembly are shown in table 4.

TABLE 4

Reassembly results overview

|  | # | % |
|---|---|---|
| Contigs (=contigs of contigs from Cap3 assembly) | 2663 |  |
| Singletons (=contigs from original Cap3 assembly) | 86771 | 93.8% |
| Contigs starting with EcoRI (=GAATTC) site | 2652 | 99.6% |
| Contigs containing internal EcoRI site | 21 | 0.8% |
| Contigs EcoRI-EcoRI | 634 | 23.8% |
| Contigs starting EcoRI and no internal EcoRI site | 2633 | 98.9% |

The generated sequence file is used to integrate with the melon genome assembly or to link the sequences to the sequence based physical map.

Average contigs length is ~500 bp.

SDSES Linkage to Sequence Based Physical Map (=WGP)

Table 7 displays the results off linking the total set of SDSES sequences to the filtered WGP tag list of melon. The total SDSES data set comprises the above mentioned through reassembly obtained contigcontigs and singletcontigs and the singleton reads remaining after the first sequence assembly round. In general it can be concluded that ~80% of the filtered melon WGP tags can be linked to at least one SDSES sequence (contig or singleton). It is also observed that in the singletons many "tags" are occurring at a high frequency. Highest value seen is 1193. Whether these are due to chloroplast/mitochondrial or repetitive sequences is unknown.

From the total SDSES sequence dataset, which contains 456369 sequences, ~59% can be linked to a WGP tag.

TABLE 7

Linkage of SDSES results to WGP melon tags

| # WGP tags used | 118414 |  |
|---|---|---|
| # WGP tags with SDSES sequences (contigs + singletons) link | 93459 | 78.9% of 118414 |
| # WGP tags with SDSES contigs link | 50895 | 43.0% of 118414 |
| # WGP tags with SDSES singleton link | 78287 | 66.1% of 118414 |
| # single SDSES sequence with WGP link | 30484 | 32.6% of 93459 |
| # single SDSES contig with WGP link | 14519 | 47.6% of 30484 |
| # single SDSES singleton with WGP link | 15965 | 52.4% of 30484 |
| # SDSES sequences (contigs + singletons) used | 456369 |  |
| # SDSES contigs used | 89404 | 86771 + 2633 |
| # SDSES singletons used | 366965 |  |
| # SDSES sequences (contigs + singletons) linked to WGP | 268755 | 58.9% of 456369 |
| # SDSES contigs linked to WGP | 61566 | 68.9% of 89404 |
| # SDSES singletons linked to WGP | 207189 | 56.5% of 366965 |
| # SDSES sequences (contigs + singletons) without WGP link | 187614 | 41.1% of 456369 |

The SDSES singleton sequences increase the coverage of the WGP tags and show that several tag sequences occur at a (very) high frequency. This indicates that assembly of the sequences can be optimized. The WGP linked SDSES contigs cover ~25 Mbp (50895 contig linked WGP tags*500 sequence length) of the melon genome. When an average contig/read length of 450 bp is used, the total WGP linked coverage of the genome is 42 Mbp (93459 WGP tags*450 bp sequence length).

The invention claimed is:

1. A method for the generation of sequence information from a DNA sample comprising
a. obtaining a sequence-based physical map of a clone bank of the DNA sample, said physical map comprising a plurality of tags each comprising remains of at least one restriction enzyme's recognition site and its neighbouring genomic sequence in the DNA sample; and
b. digesting the clone bank with the restriction enzyme of step (a) or an isoschizomer or a neoschizomer thereof and obtaining a plurality of adapter-ligated restriction fragments of the DNA sample;
c. sequencing the adapter-ligated restriction fragments;
d. anchoring the sequences of the adapter-ligated restriction fragments to the tags of the physical map of step (a).

2. The method according to claim 1, wherein the at least one restriction enzyme is a rare cutter.

3. The method according to claim 1, wherein the enzyme of step (b) is an isoschizomer of the restriction enzyme of step (a).

4. The method according to claim 1, wherein the enzyme of step (b) is the restriction enzyme of step (a).

5. The method according to claim 1, wherein step (a) comprises:
(a1) providing a clone bank comprising a plurality of clones wherein each clone contains DNA from a sample genome (or part of the sample genome);
(a2) pooling the clones from the clone bank into pools;
(a3) providing fragments for each pool using at least one restriction enzyme;
(a4) ligating first adapters to the fragments;
(a5) fragmenting the adapter-ligated restriction fragments of step (a4) to provide fragmented adapter-ligated restriction fragments and, optionally, polish one or more ends of the fragmented adapter-ligated restriction fragments;
(a6) ligating second adapters to the fragmented adapter-ligated restriction fragments to provide adapter-ligated fragmented restriction fragments, containing first and second adapters;
(a7) optionally, amplifying the adapter-ligated fragmented restriction fragments of step (a6) with a first and a second primer thereby generating amplicons;
(a8) determining the sequence of at least part of the first adapter and/or part of the fragment adjacent to the first adapter and/or of at least part of the second adapter and/or part of the fragment adjacent to the second adapter;
(a9) assigning the fragments to the corresponding clones based on the sequenced part of the first adapter and/or part of the fragment adjacent to the first adapter and/or of part of the second adapter and/or part of the fragment adjacent to the second adapter;
(a10) ordering the clones into clone-contigs thereby generating a physical map of the sample genome.

6. The method according to claim 1, wherein steps (b) and (c) are selected from the group consisting of SDSES and SDPES, wherein
I. SDSES comprises the steps of
(b1) fragmentation of a target DNA with at least one restriction endonuclease to obtain restriction fragments;
(b2) ligation of a first adapter to the ends of the restriction fragments to obtain first adapter-ligated restriction fragments;
(b3) random fragmentation of the first adapter-ligated restriction fragments to obtain randomly fragmented first adapter-ligated restriction fragments;
(b4) optionally, selection of the fragmented adapter-ligated restriction fragments that contain an adapter;
(b5) ligation of a second adapter to the fragmented ends of the first adapter-ligated restriction fragments;
(b6) optionally, amplification using a primer directed against the adapter of step (b2) and an primer directed against the second adapter of step (b5) to obtain amplified fragments;
(b7) optionally, selection of the amplified fragments obtained in step (b6) based on the presence of the second adapter;
(c1) determination of the sequence of at least part of the first adapter and/or part of the sequence of the fragment adjacent to the first adaptor and/or of at least part of the second adapter and/or part of the sequence of the fragment adjacent to the second adaptor;

II. SDPES comprises the steps of
- (b1) restriction enzyme digestion of target DNA to obtain restriction fragments;
- (b2) ligation of an IIs-adapter that contains a recognition sequence for a Type-IIs restriction endonuclease to provide IIs-adapter-ligated restriction fragments;
- (b3) fragmentation of the IIs-adapter-ligated restriction fragments to obtain fragmented IIs-adapter-ligated restriction fragments;
- (b4) circularisation of the fragmented IIs-adapter-ligated restriction fragments to obtain circularised products;
- (b5) Type-IIs restriction enzyme digestion of circularised products to provide Type-IIs digested fragments;
- (b6) ligation of a first adapter to the Type-IIs digested fragments to provide adapter-ligated Type-IIs digested fragments;
- (b7) fragmentation of the first adapter-ligated Type-IIs digested fragments;
- (b8) ligation of a second adapter to the first adapter-ligated Type-IIs digested fragments to provide first and second adapter-ligated Type-IIs digested fragments;
- (c1) determining the sequence of at least part of the fragments and/or adapters.

7. The method according to claim 6, comprising the following steps of SDSES:
- (b1) fragmentation of a target DNA with at least one restriction endonuclease to obtain restriction fragments;
- (b2) ligation of a first adapter to the ends of the restriction fragments to obtain first adapter-ligated restriction fragments;
- (b3) random fragmentation of the first adapter-ligated restriction fragments to obtain randomly fragmented first adapter-ligated restriction fragments;
- (b4) selection of the fragmented adapter-ligated restriction fragments that contain an adapter;
- (b5) ligation of a second adapter to the fragmented ends of the first adapter-ligated restriction fragments;
- (b6) amplification using a primer directed against the adapter of step (b2) and an primer directed against the second adapter of step (b5) to obtain amplified fragments;
- (b7) selection of the amplified fragments obtained in step (b6) based on the presence of the second adapter;
- (c1) determination of the sequence of at least part of the first adapter and/or part of the sequence of the fragment adjacent to the first adaptor and/or of at least part of the second adapter and/or part of the sequence of the fragment adjacent to the second adaptor.

8. The method according to claim 5, wherein the sequencing step is performed using paired end sequencing.

9. The method according to claim 5, wherein the sequencing step is performed using single end sequencing.

10. The method according to claim 6, wherein the sequencing step is performed using paired end sequencing.

11. The method according to claim 6, wherein the sequencing step is performed using single end sequencing.

12. The method according to claim 7, wherein the sequencing step is performed using paired end sequencing.

13. The method according to claim 7, wherein the sequencing step is performed using single end sequencing.

14. The method according to claim 1, further comprising generating a draft genome sequence.

* * * * *

SEQUENCE LISTING

```
<160> NUMBER OF SEQ ID NOS: 6

<210> SEQ ID NO 1
<211> LENGTH: 674
<212> TYPE: DNA
<213> ORGANISM: Cucumis melo

<400> SEQUENCE: 1
```

```
gaattcagtg gaggattgtg gggtgggttg gcgaggactc ggttttttc ggcgtcggag      60 aataaacttt ccggcgaagt ttcgccggcg atatttacag gggtttgtaa tttggaggtt    120
ttggacttgt cagagaatgc gcttttcggc ggagctccgg cggaggtttc caattgtggg    180
aatttatctt ctttgaatct gtgggggaa ccaattttct gggaagattc cggcggaaat     240
aggaagaatt cgggtttgc agaatttgta tctaggaaag aacaaatttt ctcgggaaat     300
tccagaatcc cttttgaatt tgagcaattt ggtgttcctt gatttgagca agaacaatt     360 cggaggggac attcaagaga ttttcggaag gtttacacag gtgagatttc ttgttcttca    420
tgggaatttt tacactggag ggattcattc ttctgggatt cttaagttgc caagagttgc    480
tcgtttggat ttgagtttca acaactttc aggtccattg cctgtggaaa tctctgaaat    540
gaagagcttg gagttcttga ttcttgcata taatcagttc aatggaaaca ttccatcaga    600
atatgggaac ttgaagaatc ttcaagctct tgacctttca ttcaacagct aaatgggtc    660 aatcccaaga agct                                                    674
```

<210> SEQ ID NO 2
<211> LENGTH: 586
<212> TYPE: DNA
<213> ORGANISM: Cucumis melo
<220> FEATURE:
<221> NAME/KEY: misc_feature
<222> LOCATION: (208)..(208)
<223> OTHER INFORMATION: n is a, c, g, or t

<400> SEQUENCE: 2

```
gaattcagtg gaggattgtg gggtgggttg gcgaggactc ggttttttc ggcgtcggag      60 aataaacttt ccggcgaagt ttcgccggcg atatttacag gggtttgtaa tttggaggtt    120
ttggacttgt cagagaatgc gcttttcggc ggagctccgg cggaggtttc caattgtggg    180
aatttatctt ctttgaatct gtggggnaa ccaattttct gggaagattc cggcggaaat     240
aggaagaatt cgggtttgc agaatttgta tctaggaaag aacaaatttt ctcgggaaat     300
tccagaatcc cttttgaatt tgagcaattt ggtgttcctt gatttgagca agaacaatt     360 cggaggggac attcaagaga ttttcggaag gtttacacag gtgagatttc ttgttcttca    420
tgggaatttt tacactggag ggattcattc ttctgggatt cttaagttgc caagagttgc    480
tcgtttggat ttgagtttca acaactttc aggtccattg cctgtggaaa tctctgaaat    540
gaagagcttg gagttcttga ttcttgcata taatcagttc aatgga                  586
```

<210> SEQ ID NO 3
<211> LENGTH: 507
<212> TYPE: DNA
<213> ORGANISM: Cucumis melo
<220> FEATURE:
<221> NAME/KEY: misc_feature
<222> LOCATION: (41)..(41)
<223> OTHER INFORMATION: n is a, c, g, or t

<400> SEQUENCE: 3

```
ttccaattgt gggaatttat cttctttgaa tctgtggggg naaccaattt tctgggaaga     60
ttccggcgga aataggaaga atttcgggtt tgcagaattt gtatctagga aagaacaaat    120
tttctcggga aattccagaa tccctttga atttgagcaa tttggtgttt cttgatttga    180
gcaagaacaa tttcggaggg gacattcaag agatttcgg aaggtttaca caggtgagat    240
ttcttgttct tcatgggaat ttttacactg gagggattca ttcttctggg attcttaagt    300
```

| | |
|---|---|
| tgccaagagt tgctcgtttg gatttgagtt tcaacaactt ttcaggtcca ttgcctgtgg | 360 |
| aaatctctga aatgaagagc ttggagttct tgattcttgc atataatcag ttcaatggaa | 420 |
| acattccatc agaatatggg aacttgaaga atcttcaagc tcttgacctt tcattcaaca | 480 |
| gcttaaatgg gtcaatccca agaagct | 507 |

```
<210> SEQ ID NO 4
<211> LENGTH: 507
<212> TYPE: DNA
<213> ORGANISM: Cucumis melo
<220> FEATURE:
<221> NAME/KEY: misc_feature
<222> LOCATION: (41)..(41)
<223> OTHER INFORMATION: n is a, c, g, or t

<400> SEQUENCE: 4
```

| | |
|---|---|
| ttccaattgt gggaatttgt cttctttgaa tctgtggggg naaccaattt tctgggaaga | 60 |
| ttccggcgga aataggaaga atttcgggtt tgcagaattt gtatctagga aagaacaaat | 120 |
| tttctcggga aattccagaa tcccttttga atttgagcaa tttggtgttt cttgatttga | 180 |
| gcaagaacaa tttcggaggg gacattcaag agattttcgg aaggtttaca caggtgagat | 240 |
| ttcttgttct tcatgggaat ttttacactg gagggattca ttcttctggg attcttaagt | 300 |
| tgccaagagt tgctcgtttg gatttgagtt tcaacaactt ttcaggtcca ttgcctgtgg | 360 |
| aaatctctga aatgaagagc ttggagttct tgattcttgc atataatcag ttcaatggaa | 420 |
| acattccatc agaatatggg aacttgaaga atcttcaagc tcttgacctt tcattcaaca | 480 |
| gcttaaatgg gtcaatccca agaagct | 507 |

```
<210> SEQ ID NO 5
<211> LENGTH: 759
<212> TYPE: DNA
<213> ORGANISM: Cucumis melo

<400> SEQUENCE: 5
```

| | |
|---|---|
| gaacaaaaag aataacatac agccgcataa cacacacgct ttcaatccta gtattttttct | 60 |
| ttttcttcgt cgcacaatac aaatgcacaa ggcaaataaa aagaccacac aaataaggaa | 120 |
| agaccatcaa ctggccataa ggaccaccca caacaatatg accaaagcaa taaggaaagt | 180 |
| taaagcatgg gaacaaaata caacgacttt tttactgcca accaaaaagt aatttataag | 240 |
| caccttttgaa taagttaact attcaataat ttatacaaaa ttaattaaca tctatgatga | 300 |
| actcgtaggt ttatcagcaa ctggagtttc atattcagat tcgaaaggaa agttacacac | 360 |
| agcatccatt cacaaaaatg gtgagataat tgtaagtgca ggagccattg gaagtcctca | 420 |
| acttctcctt ctaagtggaa ttggcccgaa atctcatctt tcatccttaa aactacctgt | 480 |
| cgttcttcac caacctcacg tcggacagtt tatgacggac aacattgtcc ttccattcca | 540 |
| attacttcct tcagctggaa aagttgtcgg aattttacaa gatccccgtt tcggtaccac | 600 |
| aaatatctat atacaatctt tcgctggccc ttcaacattt ttagttccac cagctttcag | 660 |
| cctccttcct cctcaatcca cttccatcaa ccccaccttta gcaagttttg ttggtaaatt | 720 |
| ctctgatgtc aattctaaag ggtggcttca tttgaattc | 759 |

```
<210> SEQ ID NO 6
<211> LENGTH: 759
<212> TYPE: DNA
<213> ORGANISM: Cucumis melo

<400> SEQUENCE: 6
```

```
gaacaaaaag aataacatac agccgcataa cacacacgct ttcaatccta gtatttttct      60
ttttcttcgt cgcacaatac aaatgcacaa ggcaaataaa aagaccacac aaataaggaa     120
agaccatcaa ctggccataa ggaccaccca caacaatatg accaaagcaa taaggaaagt     180
taaagcatgg gaacaaaata acaacgactt tttactgcca accaaaaagt aatttataag     240 caccttttgaa taagttaact attcaataat ttatacaaaa ttaattaaca tctatgatga    300
actcgtaggt ttatcagcaa ctggagtttc atattcagat tcgaaaggaa agttacacac    360
agcatccatt cacaaaaatg gtgagataat tgtaagtgca ggagccattg gaagtcctca    420
acttctcctt ctaagtggaa ttggcccgaa atctcatctt tcatccttaa aactacctgt    480
cgttcttcac caacctcacg tcggacagtt tatgacggac aatccccgtt tcggtaccac   540
cattgtcctt ccattccaat tacttccttc agctggaaaa gttgtcggaa ttttacaaga    600
aaatatctat atacaatctt tcgctggccc ttcaacattt ttagttccac cagctttcag   660
cctccttcct cctcaatcca cttccatcaa ccccaccta gcaagttttg ttggtaaatt    720
ctctgatgtc aattctaaag ggtggcttca tttgaattc                          759
```